(12) United States Patent
Tabatadze et al.

(10) Patent No.: US 9,617,535 B2
(45) Date of Patent: *Apr. 11, 2017

(54) OLIGONUCLEOTIDE COMPLEX COMPOSITIONS AND METHODS OF USE AS GENE ALTERATION TOOLS

(71) Applicant: The General Hospital Corporation, Boston, MA (US)

(72) Inventors: David R. Tabatadze, Worcester, MA (US); Paul C. Zamecnik, Boston, MA (US); Malay K. Raychowdhury, Lexington, MA (US); Horacio F. Cantiello, Rowley, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 12 days.

This patent is subject to a terminal disclaimer.

(21) Appl. No.: 14/458,952

(22) Filed: Aug. 13, 2014

(65) Prior Publication Data

US 2015/0284708 A1 Oct. 8, 2015

Related U.S. Application Data

(63) Continuation of application No. 13/418,998, filed on Mar. 13, 2012, now Pat. No. 8,841,271, which is a continuation of application No. 10/594,829, filed as application No. PCT/US2005/010744 on Mar. 29, 2005, now Pat. No. 8,314,226.

(60) Provisional application No. 60/560,026, filed on Apr. 7, 2004, provisional application No. 60/557,732, filed on Mar. 29, 2004.

(51) Int. Cl.
| | | |
|---|---|---|
| *C12N 15/11* | (2006.01) | |
| *C12N 15/10* | (2006.01) | |
| *C12N 15/113* | (2010.01) | |
| *A61K 48/00* | (2006.01) | |

(52) U.S. Cl.
CPC ....... *C12N 15/102* (2013.01); *C12N 15/1024* (2013.01); *C12N 15/113* (2013.01); *A61K 48/00* (2013.01); *C07K 2319/07* (2013.01); *C07K 2319/10* (2013.01); *C12N 2310/11* (2013.01); *C12N 2310/315* (2013.01); *C12N 2310/321* (2013.01); *C12N 2310/346* (2013.01); *C12N 2310/3519* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 5,149,797 A | 9/1992 | Pederson et al. | |
| 5,565,350 A | 10/1996 | Kmiec | |
| 5,627,274 A | 5/1997 | Kole et al. | |
| 5,856,092 A | 1/1999 | Dale et al. | |
| 8,314,226 B2 * | 11/2012 | Tabatadze | 536/24.5 |
| 8,841,271 B2 * | 9/2014 | Tabatadze | 514/44 R |
| 2002/0064876 A1 | 5/2002 | Yoon | |
| 2002/0119570 A1 | 8/2002 | Yoon et al. | |
| 2003/0051270 A1 | 3/2003 | Kmiec et al. | |
| 2003/0109476 A1 | 6/2003 | Kmiec et al. | |
| 2003/0196218 A1 | 10/2003 | Arntzen et al. | |
| 2003/0199091 A1 | 10/2003 | Kmiec et al. | |
| 2003/0217377 A1 | 11/2003 | Kmiec et al. | |
| 2004/0014057 A1 | 1/2004 | Kmiec et al. | |
| 2004/0023903 A1 | 2/2004 | Davis et al. | |

FOREIGN PATENT DOCUMENTS

WO WO-9619587 A2 6/1996

OTHER PUBLICATIONS

Agrawal et al. "Antisense and/or Immunostimulatory Oligonucleotide Therapeutics." *Curr. Cancer Drug Targets.* 1.3(2001):197-209.

Agrawal et al. "Mixed Backbone Oligonucleotides: Improvement in Oligonucleotide-induced Toxicity In Vivo." *Antisense Nucleic Acid Drug Dev.* 8.2(1998):135-139.

Agrawal et al. "Site-Specific Excision from RNA by RNase H and Mixed-Phosphate-Backbone Oligodeoxynucleotides." *PNAS.* 87(1990):1401-1405.

Alexeev et al. "Simultaneous Targeted Alteration of the Tyrosinase and C-kit Genes by Single-Stranded Oligonucleotides." *Gene Ther.* 9(2002):1667-1675.

Alexeev et al. "Stable and Inheritable Changes in Genotype and Phenotype of Albino Melanocytes Induced by an RNA-DNA Oligonucleotide." *Nat. Biotech.* 16.13(1998):1343-1346.

Andersen et al. "Mechanisms Underlying Targeted Gene Correction Using Chimeric RNA/DNA and Single-Stranded DNA Oligonucleotides." *J Mol. Med.* 80(2002):770-781.

Anderson et al. "Generation of cAMP-activated Chloride Currents by Expression of CFTR." *Science.* 251(1991):679-682.

Arispe et al. "Direct Activation of Cystic Fibrosis Transmembrane Conductance Regulator Channels by 8-Cyclopentyl-1,3-dipropylxanthine (CPX) and 1,3-Diallyl-8-cyclohexylxanthine (DAX)." *J. Biol. Chem.* 273(1998):5727-3574.

Bear et al. "Purification and Functional Reconstitution of the Cystic Fibrosis Transmembrane Conductance Regulator (CFTR)." *Cell.* 68(1992):809-818.

Bedwell et al. "Suppression of a CFTR Premature Stop Mutation in a Bronchial Epithelial Cell Line." *Nat. Med.* 3(1997):1280-1284.

Bernstein et al. "Role for a Bidentate Ribonuclease in the Initiation Step of RNA Interference." *Nature.* 409(2001):363-366.

Boucher et al. "Gene Therapy for Cystic Fibrosis Using E1-Deleted Adenovirus: A Phase I Trial in the Nasal Cavity." *Hum. Gene Ther.* 5(1994):615-639.

(Continued)

Primary Examiner — Jim Ketter
(74) Attorney, Agent, or Firm — Mintz Levin Cohn Ferris Glovsky and Popeo, P.C.

(57) ABSTRACT

Compositions and methods of treatments of cells are provided for altering the phenotype of a cell by administering an oligonucleotide complex to the cell, the complex having two strands and chemical modifications.

10 Claims, 21 Drawing Sheets

(56) References Cited

OTHER PUBLICATIONS

Figure 1:
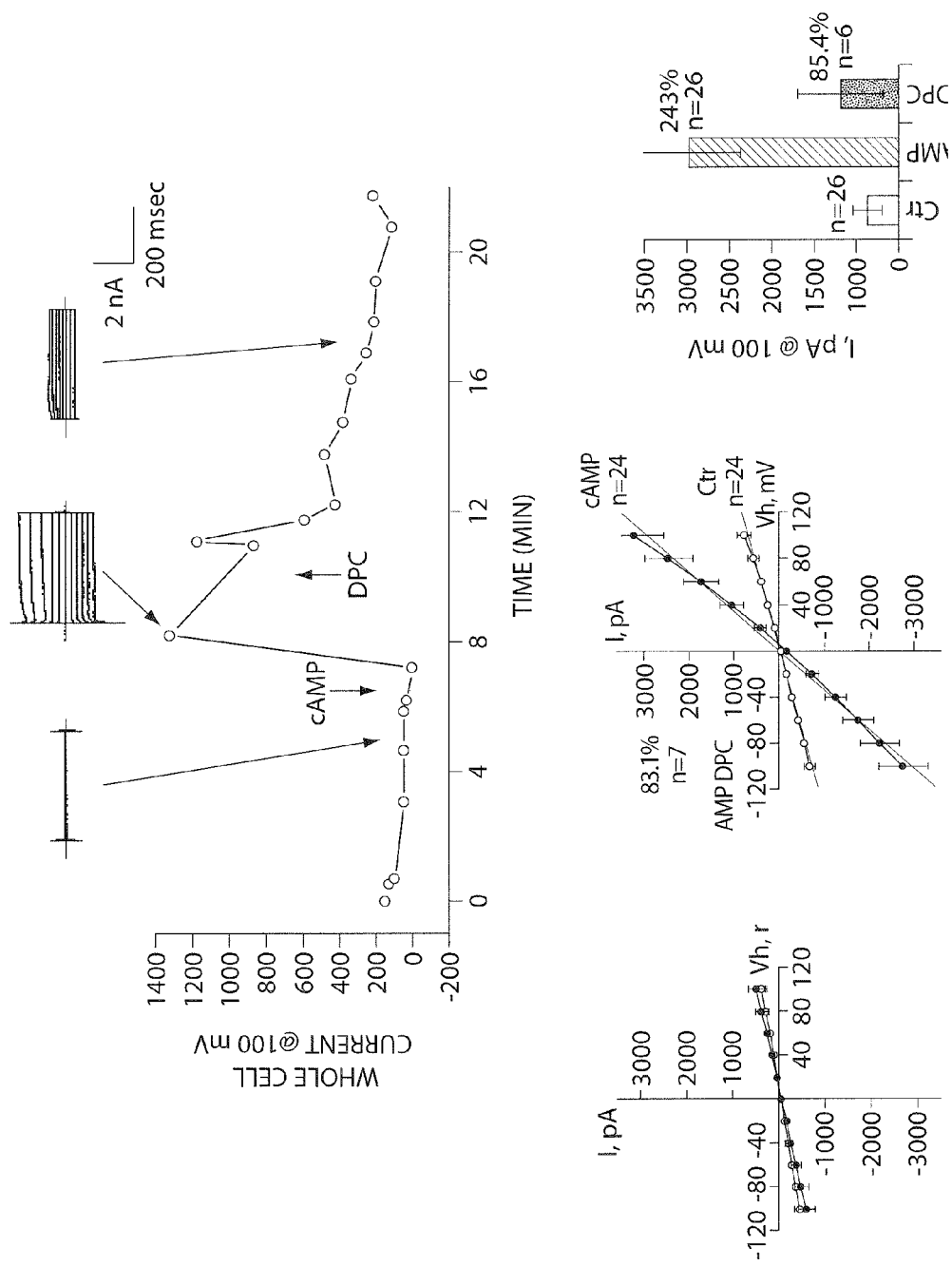

Breschel et al. "A Novel, Heritable, Expanding CTG Repeat in an Intron of the SEF2-1 Gene on Chromosome 18q21.1." *Human Molec. Gen.* 6(1997):1855-1863.
Brown et al. "Chemical Chaperones Correct the Mutant Phenotype of the ΔF508 Cystic Fibrosis Transmembrane Conductance Regulator Protein." *Cell Stress Chaperones.* 1(1996):117-125.
Burkard et al. "Structures of Base Pairs Involving at Least Two Hydrogen Bonds." *In the RNA World.* Gesteland et al., eds. New York: Cold Spring Harbor Press. 2nd ed.(1999):675-680.
Burke. "Genomic Medicine: Genomics as a Probe for Disease Biology." *N. Eng. J. Med.* 349(2003):969-974.
Cantiello et al. "External ATP and its Analogs Activate the Cystic Fibrosis Transmembrane Conductance Regulator by a Cyclic AMP-Independent Mechanism." *J. Biol. Chem.* 269(1994):11224-11232.
Cheng et al. "Defective Intracellular Transport and Processing of CFTR is the Molecular Basis of Most Cysic Fibrosis." *Cell.* 63(1990):827-834.
Cole-Strauss et al. "Correction of the Mutation Responsible for Sickle Cell Anemia by an RNA-DNA Oligonucleotide." *Science.* 273(1996):1386-1389.
Crawford et al. "Immunocytochemical Localization of the Cystic Fibrosis Gene Product CFTR." *PNAS.* 88.20(1991):9262-9266.
Cutting. "Spectrums of Mutations in Cystic Fibrosis." *J. Bioenerg. Biomembr.* 25(1993):7-10.
Dechecchi et al. "Protein Kinease C Activates Chloride Conductance in C127 Cells Stably Expressing the Cystic Fibrosis Gene." *J. Biol. Chem.* 268(1993):11321-11325.
Denning et al. "Processing of Mutant Cystic Fibrosis Transmembrane Conductance Regulator is Temperature-Sensitive." *Nature.* 358(1992):761-764.
Du et al. "Identification of *Aim-a* as the *underwhite* Mouse Mutant and its Transcriptional Regulation by MITF." *J. Biol. Chem.* 277.1(2002):402-406.
Felsenfeld et al. "Formation of a Three-Stranded Polynucleotide Molecule." *J. Am. Chem. Soc.* 79(1957):2023-2024.
Ferrie et al. "Development, Multiplexing, and Application of ARMS Tests for Common Mutations in the CFTR Gene." *Am. J. Hum. Genet.* 51(1992): 251-262.
Fire et al. "Potent and Specific Genetic Inference by Double-Stranded RNA in *Caenorhabditis elegans.*" *Nature.* 391(1998):806-811.
Gilfillan et al. "P67L: A Cystic Fibrosis Allele with Mild Effects Found at High Frequency in the Scottish Population." *J. Med. Genet.* 35(1998):122-125.
Grishok et al. "Genetic Requirements for Inheritance of RNAi in *C. elegans.*" *Science.* 287(2000):2494-2497.
Hammond et al. "An RNA-Directed Nuclease Mediates Post-Transcriptional Gene Silencing in *Drosphila* Cells." *Nature.* 404(2000):293-296.
Hannon. "RNA Interference." *Nature.* 418(2002):244-251.
Harris et al. "Distribution and Consenus of Branch Point Signals in Eukaryotic Genes: A Computerized Statistical Analysis." *Nucleic Acid Res.* 18(1990):3015-3019.
Igoucheva et al. "Targeted Gene Correction by Small Single-Stranded Oligonucleotides in Mammalian Cells." *Gene Ther.* 8.5(2001):391-399.
Jurica et al. "Pre-mRNA Splicing." *Mol. Cell.* 12.1(2003):5-14.
Kandimalla et al. "Toll-like Receptor 9: Modulation of Recognition and Cytokine Induction by Novel Synthetic CpG DNAs." *Biochem. Soc. Trans.* 31.Pt3(2003):654-658.
Kerem et al. "Identification of the Cystic Fibrosis Gene: Genetic Analysis." *Science.* 245(1989):1073-1080.
Kleppe et al. "Studies on Polynucleotides." *J. Mol. Biol.* 56.2(1971):341-361.
Kmiec. "Targeted Gene Repair." *Clin. Invest.* 112(2003):632-636.
Knauert et al. "Triplex Forming Oligonucleotides: Sequence-Specific Tools for Gene Targeting." *Hum. Mol. Genet.* 10(2001):2243-2251.
Kobayashi et al. "Benign Missense Variations in the Cystic Fibrosis Gene." *Am. J. Hum. Genet.* 47(1990):611-615.
Krieg. "CpG Motifs: The Active Ingredient in Bacterial Extracts?" *Nat. Med.* 9(2003):831-835.
Letsinger et al. "Use of a Steroid Cyclic Disulfide Anchor in Constructing Gold Nanoparticle-Oligonucleotide Conjugates." *Bioconj. Chem.* 11(2000):289-291.
Li et al. "The Cystic Fibrosis Mutation (F508) does not Influence the Chloride Channel Activity of CFTR." *Nature Genet.* 3(1993):311-316.
Liu et al. "Partial Correction of Endogenous F508 CFTR in Human Cystic Fibrosis Airway Epithelia by Spliceosome-Mediated RNA Trans-Splicing." *Biotechnol.* 20(2002):47-52.
MacDonald et al. "A Novel Gene Containing a Trinucledotide Repeat That is Expanded and Unstable on Huntington's Disease Chromosomes." *Cell.* 72(1993):971-983.
Mansfield et al. "Repair of CFTR mRNA by Spliceosome-Mediated RNA Trans-Splicing." *Gene Ther.* 7(2000):1885-1895.
McManus et al. "Gene Silencing in Mammals by Small Interfering RNAs." *Nat. Rev Genet.* 3(2003):737-747.
Metelev et al. "Study of Antisense Oligonucleotide Phosphorothioates Containing Segments of Oligodeoxynucleotides and 2'-o-Methyloligoribonucleotides." *Bioorg. Med. Chem. Lett.* 4(1994):2929-2934.
Montgomery et al. "RNA as a Target of Double-Stranded RNA-Mediated Genetic Interference in *Aenorhabditis elegans.*" *PNAS.* 95(1998):15502-15507.
Nielsen. "Targeting Double Stranded DNA with Peptide Nucleic Acid (PNA)." *Curr. Med. Chem.* 8(2001):545-550.
Onay et al. "Analysis of the CFTR Gene in Turkish Cystic Fibrosis Patients: Identification of Three Novel Mutations (3172de1AC, P1013L, and M1028I)." *Hum. Genet.* 102(1998):224-230.
Padmapriya et al. "Large-Scale Synthesis, Purification, and Analysis of Oligodeoxynucleotide Phosphorothioates." *Antisense Res Dev.* 4(1994):185-199.
Parekh-Olmedo et al. "Targeted Gene Repair in Mammalian Cells Using Chimeric RNA/DNA Oligonucleotides and Modified Single-Stranded Vectors." *Sci. STKE.* 73(2001):PL1.
Pasyk et al. "Mutant (δF508) Cystic Fibrosis Transmembrane Conductance Regulator CI-Channel is Functional When Retained in Endoplasmic Reticulum of Mammalian Cells." *J. Biol. Chem.* 270(1995):12347-12350.
Pickles. "Physical and Biological Barriers to Viral Vector-Mediated Delivery of Genes to the Airway Epithelium." *Proc. Am. Thorac. Soc.* 1.4(2004):302-308.
Puttaraju et al. "Messenger RNA Repair and Restoration of Protein Function by Spliceosome-Mediated RNA *Trans*-Splicing." *Mol. Ther.* 4(2001):105-114.
Ram et al. "CI—Permeability of Human Sweat Duct Cells Monitored with Fluorescence-Digital Imaging Microscopy: Evidence for Reduced Plasma Membrane CI—Permeability in Cystic Fibrosis." *PNAS.* 86(1989):10166-10170.
Reisin et al. "The Cystic Fibrosis Transmembrane Conductance Regulator is a Dual ATP and Chloride Channel." *J. Biol. Chem.* 269(1994):20584-20591.
Richardson et al. "Strategies for Hepatic Gene Correction." *J. Drug Target.* 10(2002):133-134.
Riordan et al. "Identification of the Cystic Fibrosis Gene: Cloning and Characterization of Complementary DNA." *Science.* 245(1989):1066-1073.
Rose et al. "Blood Gas-Analyses in Patients with Cystic Fibrosis to Estimate Hypoxemia During Exposure to High Altitudes in a Hypobaric-Chamber." *Eur.J. Med. Res.* 5.1(2000):9-12.
Shen et al. "Impact of Mixed-Backcone Oligonucleotides on Target Binding Affinity and Target Cleaving Specificity and Selectivity by *Escherichia coli* RNase H." *Bioorg. Med. Chem.* 6.10(1998):1695-1705.
Silva et al. "RNA Interference: A Promising Approach to Antiviral Therapy." *Trends Mol. Med.* 8(2002):505-508.
Simpson et al. "RNA Editing." *Annu. Rev. Neurosci.* 19(1996):27-52.
Sioud. "RNA Interference and Innate Immunity." *Adv. Drug Deliv. Rev.* 59.2-3(2007):153-163.

(56) References Cited

OTHER PUBLICATIONS

Skerra. "Phosphorothioate Primers Improve the Amplification of DNA Sequences by DNA Polymerases with Proofreading Activity." *Nucleic Acid Res.* 20(1992):3551-3554.

Smith et al. "Generating a Synthetic Genome by Whole Genome Assembly: ωX174 Bacteriophage from Synthetic Oligonucleotides." *PNAS.* 100(2003):15440-15445.

Spector. "Nuclear Organization of Pre-mRNA Processing." *Curr. Opin. Cell Biol.* 5(1993):442-447.

Stephenson et al. "Inhibition of Rous Sarcoma Viral RNA Translation by a Specific Oligodeoxynucleotide." *PNAS.* 75(1978):285-288.

Strandvik et al. "Spectrum of Mutations in the CFTR Gene of Patients with Classical and Atypical Forms of Cystic Fibrosis from Southwestern Sweden: Identification of 12 Novel Mutations." *Genet. Test.* 5(2001):235-242.

Taton et al. "Scanometric DNA Array Detection with Nanoparticle Probes." *Science.* 289(2000):1757-1759.

Taubes. "The Strange Case of Chimeraplasty." *Science.* 298(2002):2166-2120.

Temsamani et al. "Inhibition of in vitro Transcription by Oligodeoxynucleotides." *Antisense Res. Dev.* 4(1994):279-284.

Teramoto et al. "Factors Influencing Adeno-Associated Virus-Mediated Gene Transfer to Human Cystic Fibrosis Airway Apithelial Cells: Comparison with Adenovirus Vectors." *J. Virol.* 72(1998):8904-8912.

Thuong et al. "Sequence-Specific Recognition and Modification of Double-Helical DNA by Oligonucleotides." *Angw. Chem Intl. Ed. Eng.* 32.5(1993):666-690.

Tsui. "The Spectrum of Cystic Fibrosis Mutations." *Trends Genet.* 8.11(1992):392-398.

Verkman. "Development and Biological Applications of Chloride-Sensitive Fluorescent Indicators." *Am. J. Physiol.* 259(1990):C375-C388.

Visich et al. "Complete Screening of the CFTR Gene in Argentine Cystic Fibrosis Patients." *Clin. Genet.* 61(2002):207-213.

Wang et al. "DNA Bending and Unbending by MutS Govern Mismath Recognition and Specificity." *PNAS.* 100(2003):14822-14827.

Ward et al. "Intracellular Turnover of Cystic Fibrosis Transmembrane Conductance Regulator." *J. Biol. Chem.* 269(1994):25710-25718.

Welsh et al. "Molecular Mechanisms of CFTR Chloride Channl Dysfunction in Cystic Fibrosis." *Cell.* 73(1993):1251-1254.

Wu et al. "Prospects of Chimeric RNA-DNA Oligonucleotides in Gene Therapy." *J. Biomed. Sci.* 8.6(2001):439-445.

Yang et al. "Crystal Structures that Suggest Late Development of Genetic Code Components for Differentiating Aromatic Side Chains." *PNAS.* 100(2003):15376-15380.

Yoon et al. "Targeted Gene Correction of Episomal DNA in Mammalian Cells Mediated by a Chimeric RNA.DNA Oligonucleotide." *PNAS.* 93(1996):2071-2076.

Zamecnik et al. "History of Anti-Sense Oligonucleotides." *Antisense Therapeutics.* Agrawal, ed. N.J.: Humana Press. (1996):1-11 (1996).

Zamecnik et al. "Inhibition of Rous Sarcoma Virus Replication and Cell Transformation by a Specific Oligodeoxynucleotide." *PNAS.* 75.1(1978):280-284.

Zamore et al. "RNAi: Double-Stranded RNA Directs the ATP-Dependent Cleavage of mRNA at 21 to 23 Nucleotide Intervals." *Cell.* I01.1(2000)25-33.

Zhang et al. "Failure to Achieve Gene Conversion with Chimeric Circular Oligonucleotides: Potentially Misleading PCR Artifacts Observed." *Antisense Nucleic Acid Drug Dev.* 8.6(1998):531-536.

* cited by examiner

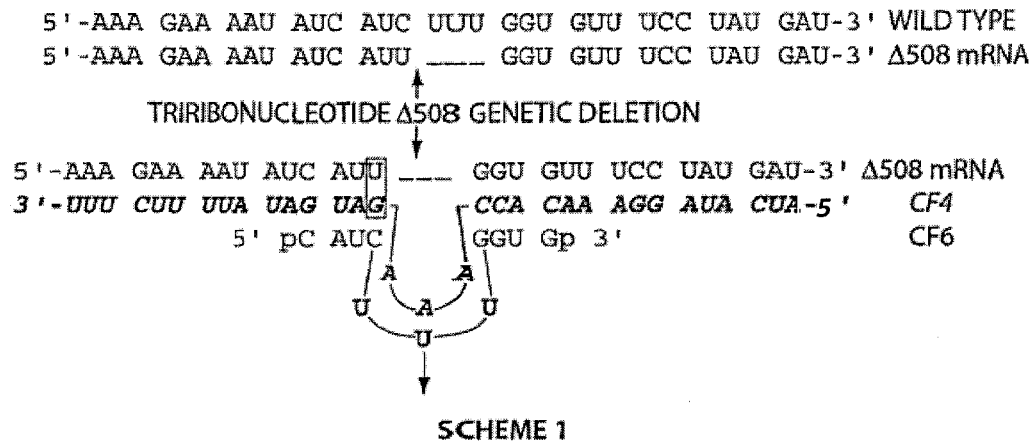

Δ508 mRNA REPAIR:
    5'-AAA GAA AAU AUC AUC UUU GGU GUU UCC UAU GAU-3'  WILD TYPE
    5'-AAA GAA AAU AUC AUU ___ GGU GUU UCC UAU GAU-3'  Δ508 mRNA
                    ↑
    TRIRIBONUCLEOTIDE Δ508 GENETIC DELETION
                    ↓
    5'-AAA GAA AAU AUC AUU ___ GGU GUU UCC UAU GAU-3'  Δ508 mRNA
    3'-UUU CUU UUA UAG UAG    CCA CAA AGG AUA CUA-5'   CF4
               5' pC AUC      GGU Gp 3'                CF6
                       A    A
                       U  A  U
                          U
                          ↓

SCHEME 1

Fig. 7A

VARIED RIBONUCLEOTIDE INSERTION AND DELETION STEPS, WITH (c) BEING THE BEST RESULT):
                          ↓

REPEATED SEQUENCE ANALYSIS OF RT-PCR PRODUCTS WITH DIFFERENT PRIMERS:
(a) ARMS REVERSE PRIMER (N1)
    5'-AAA GAA AAU AUC A ___ UGU GGU GUU UCC UAU GAU-3'

(b) ARMS FORWARD PRIMER (NF1)
    5'-AAA GAA AAU AUC AUC UGU ___ GUU UCC UAU GAU-3'

(c) ARMS FORWARD PS PRIMER (SNF1)
    5'-AAA GAA AAU AUC AUC UGU GGU GUU UCC UAU GAU-3'

SCHEME 1

Fig. 7B

SCHEME 3

SCHEME 4

SCHEME 5

SCHEME 6

SCHEME 7

SCHEME 8

SCHEME 10

SEQUENCE OF mRNA FROM -12 POSITION

```
      ↓-12           ↓+1                          mRNA              ↓+30
5'  CGG GAG ACC GCC AUG GCG ACC CUG GAA AAG CUG AUG AAG GCC  3'
3'  GCC CTC TGG CGG TAC CGC TGG GAC CTT TTC GAC TAC TTC CGG  5'
                                                    ANTISENSE
```

MECHANISM OF DELETION/INSERTION:

STEP 1 - ADDITION OF RNase H ACTIVATING OLIGONUCLEOTIDE (OLIGONUCLEOTIDE IDENTITY (ID) IS HT3)

mRNA
```
5'  CGG GAG ACC GCC AUG GCG ACC CUG GAA AAG CUG AUG AAG GCC  3'
3'                   CGC  TGG GTC CTT TTC GAC     (HT3)   5'
```

STEP 2 - ADDITION OF INSERTION DUPLEX (DUPLEX ID:HT4/HT6)

CUT mRNA
```
5'...CGG GAG ACC GCC AUG GCG                 CUG AUG AAG GCC...3'
3'   (HT4)   TGG CGG TAC CGC TGG ATT TT -xGAC TAC TTC CGG   5'
5'   (HT6)                    pACC UAA AAp                  3'
```

INSERTED mRNA
```
5'...CGG GAG ACC GCC AUG GCG  ACC UAA AA  CUG AUG AAG GCC...3'
```

WILD TYPE mRNA (5'>3')
CGG GAG ACC GCC AUG GCG ACC CUG GAA AAG CUG AUG AAG GCC

MODIFIED mRNA
CGG GAG ACC GCC AUG GCG ACC ___ UAA ___ AAx CUG AUG AAG GCC

DELETED BASE

SCHEME 15

Fig. 21

AIM-1 ALLELE OF MATP

MUTATED DUPLEX
5' AGC AGG ACC CTC AGG GCT-GTC AGC CAG TGG GAT GCA 3'
3' TCG TCC TGG GAG TCC CGA-CAG TCG GTC ACC CTA CGT 5'

WILD TYPE
5' AGG ACC CTC AGG GCT CGT CGC T GTC AGC CAG TGC GAT GCA 3'
3' TCC TGG GAG TCC CGA GCA GCG A CAG TCG GTC ACG CTA CGT 5'

MECHANISM OF DELETION/INSERTION:

MUTATED mRNA
5' AGC AGG ACC CUC AGG GCU GUC AGC CAG UGG GAU GCA 3'
       3' [UCC] CGA CAG [UCG] 5' (OLIGOS ID: Alb 3)

5' AGC AGG ACC CTC AGG-------AGC CAG TGG GAT GCA 3'
       3' [UCC] CGA CAG [UCG] 5' (OLIGOS ID: Alb 3)

Alb 4/Alb 6 DUPLEX ADDED

5' pGCU CGU CGC U GUCp 3' Alb6
3' UGG GAG UCC CGA GCA GCG A CAG UCG GUC ACC 5' Alb 4

REPAIRED mRNA
5' AGC AGG ACC CUC AGG GCU CGU CGC U GUC AGC CAG UGG GAU GCA

SCHEME 16

Fig. 22

OLIGONUCLEOTIDE COMPLEX COMPOSITIONS AND METHODS OF USE AS GENE ALTERATION TOOLS

CROSS-REFERENCE TO RELATED APPLICATIONS

This application is a continuation of U.S. patent application Ser. No. 13/418,998, now U.S. Pat. No. 8,841,271, filed Mar. 13, 2012, which is a continuation of U.S. patent application Ser. No. 10/594,829, now U.S. Pat. No. 8,314,226, filed Dec. 19, 2007, which is a National Phase entry of International Patent Application No. PCT/US05/010744, filed Mar. 29, 2005, which claims the priority benefit of U.S. Provisional Patent Application No. 60/560,026, filed Apr. 7, 2014, and U.S. Provisional Patent Application No. 60/557,732, filed Mar. 29, 2004, the disclosures of each of which are incorporated by reference herein in their entireties.

TECHNICAL FIELD

The present invention relates to the use of specific complexes of oligonucleotides and their modification products as therapeutic and/or prophylactic agents for the phenotypic and/or genotypic restoration of mutated genes, genes with inborn errors and/or for switch-on and/or switch-off of targeted gene(s).

BACKGROUND OF INVENTION

Numerous genetic diseases are caused by mutations in the mammalian genome. Other sources of genetic diseases are activation of silent genes or the presence of viral genes in the mammalian genome. Several types of modifications have been found to be mutated in the genome: deletion of one or several base pairs, one or several mismatches in the sequence of the gene, insertion of one or several bases, or repeat triplet reiteration and absence of a whole or part of a gene.

Genetic diseases caused by mismatches, deletion/insertion of one or several base pairs (BP) and repeat triplet mutation in the genes include albinism, cystic fibrosis, muscular dystrophy and atrophy, sickle cell anemia, hepatic disorders, hemophilia, Crigler-Najjar syndrome, renal tubular acidosis, β-thalassemia, atherosclerosis, Huntington's disease, spinocerebellar ataxia (type 1, 2 and 6), Machado-Joseph disease, myotonic dystrophy, Fragile X (forms A and B) and Frederich's ataxia [Breschel et al., Human Molec. Gen. (1997) 6, 1855-1863; Kmiec, Clin. Invest. (2003) 112, 632-636].

Oligonucleotide complexes and their analogs have been employed as a potential therapeutic for the readout of genes [McManus et al., Nat Rev Genet. (2002) 3, 737-747; Nielsen, Curr. Med. Chem. (2001) 8, 545-550; Agrawal et al., Curr. Cancer Drug Targets. (2001) 1, 197-209] and for targeted gene repair [Kmiec, Clin. Invest. (2003) 112, 632-636].

An approach in the field of gene therapy is introduction of sequence-specific modification of the genes, using oligonucleotide complexes for the phenotypic and/or genotypic restoration of defective genes. Approaches to an oligonucleotide-based strategy to achieve this goal have been tested. Chimeric RNA/DNA oligonucleotides and single-stranded oligonucleotides were developed for site-specific correction of episomal and chromosomal target genes [Andersen et al. J Mol Med. (2002) 80, 770-81; Alexeev et al., Gene therapy (2002) 9, 1667-1675; Kmiec, Clin. Invest. (2003) 112, 632-636; Wu et al., J Biomed Sci. (2001) 8, 439-45; Yoon, U.S. Patent Application Publication 1999000473872; Davis et al., U.S. Patent Application Publication 2000767775; Youn el al., U.S. Patent Application Publication 2001000962628; Kmiec et al., U.S. Patent Application Publication 2002000260375; Kmiec et al., U.S. Patent Application Publication 2002000215432]. Experiments demonstrated the feasibility of using chimeric RNA/DNA and single stranded oligonucleotides to introduce point conversions in genes in vitro and in vivo. This gene repair approach relies on hybridization of the chimera to the target gene, generating a mismatch with the targeted point mutation. Restored gene function was anticipated to occur through activation of endogenous repair systems that recognize the created mismatch [Andersen et al., J Mol Med. (2002) 80, 770-81; Alexeev et al., Gene therapy (2002) 9, 1667-1675; Kmiec, Clin. Invest. (2003) 112, 632-636; Wu et al., J Biomed Sci. (2001) 8, 439-45; Wang et al., (2003) Proc. Natl. Acad. Sci. USA 100, 14822-14827]. Double stranded oligonucleotides have been tested for site specific gene alteration in plant cells [Arntzen et al., U.S. Patent Application Publication 1998000129298; Kmiec, U.S. Patent Application Publication 1994000353657].

Triplex forming oligonucleotides also have been employed as sequence-specific tools for gene targeting. Triplex forming oligonucleotides bind in the major groove of double stranded DNA, with high affinity. Because of this characteristic, triplex forming oligonucleotides have been proposed as tools for the site specific corrections of targeted genes [Knauert et al., Hum Mol Genet. (2001) 10, 2243-2251; Richardson et al., Drug Target (2002) 10, 133-134; Thoung et al., (1993) Angewandte Chemie. Intl. Ed. Eng., 32, 666-690.].

Current targeted gene repair methods are controversial and still at the level of development. There is a need for more effective tools, in order to obtain phenotypic or genotypic restoration of defective genes in somatic tissues.

SUMMARY OF THE INVENTION

The present invention is directed to a method for targeted gene repair. The method is carried out by contacting a non-repaired target RNA with an RNA oligonucleotide complex containing a first oligonucleotide and a second oligonucleotide, the first oligonucleotide containing a sequence complementary to a repaired target RNA, wherein the RNA sequence of the first oligonucleotide contains an RNase H-resistant modification, and the second oligonucleotide contains an RNA sequence complementary to at least 6 nucleotides of the first oligonucleotide at the site on the sequence of the first oligonucleotide which is not complementary to the non-repaired target RNA; and hybridizing the complex to the non-repaired target RNA in the presence of an RNase, thereby producing a repaired RNA. The first oligonucleotide and the second oligonucleotide are annealed. The repaired target RNA is a wild-type sequence of a gene or another desired reference sequence. The sequence of non-repaired target RNA differs from that of the repaired or wild type sequence. For example, the non-repaired target RNA is a mutated sequence compared to the wild type or desired reference sequence. In a preferred embodiment, mutation is a substitution, deletion or insertion of at least one base pair compared to a normal wild type sequence. Prior to contacting a non-repaired target RNA with an RNA oligonucleotide complex the non-repaired target RNA is contacted with a phosphorothioate (PS) containing sequence comprising a deoxynucleotide with RNase H resistant flanking ends.

For example, the RNase H-resistant modification is the addition of a 2'-O-methyl moiety.

The first oligonucleotide is preferably at least 10 nucleotides in length, e.g. the first oligonucleotide contains about 33 nucleotides. The second oligonucleotide comprises at least 7 nucleotides, the second oligonucleotide comprises about 11 nucleotides.

The step of, contacting the target RNA preferably occurs within a cell. The cell is in vitro, ex vivo or in vivo. The cell is a mammalian cell such as a human cell or an animal cell such as a dog, cat, horse, cow, sheep, or other domesticated or wild animal.

The present invention is directed to a method for treating or ameliorating cystic fibrosis in a subject in need thereof, comprising administering an RNA oligonucleotide complex directed to a non-repaired target RNA, the complex comprising a first oligonucleotide and a second oligonucleotide, the first oligonucleotide comprising a sequence complementary to a repaired target RNA, wherein the RNA sequence of the first oligonucleotide comprises an RNase H-resistant modification, and the second oligonucleotide comprises an RNA sequence complementary to at least 6 nucleotides of the first oligonucleotide at the site on the sequence of the first oligonucleotide which is not complementary to the non-repaired target RNA; and wherein administration produces a repaired targeted RNA, thereby treating or ameliorating cystic fibrosis. The first oligonucleotide and the second oligonucleotide are annealed.

The repaired target RNA is a wild-type sequence. In another embodiment, the non-repaired target RNA is a mutated sequence compared to a reference desired sequence. For example a mutated sequence includes a substitution, deletion or insertion of at least one base pair compared to a normal wild type sequence.

Prior to administering an RNA oligonucleotide complex, a phosphorothioate (PS) containing sequence comprising a deoxynucleotide with RNase H resistant flanking ends is administered. In an example, the RNase H-resistant modification is the addition of a 2'-O-methyl moiety. The first oligonucleotide is typically at least 10 nucleotides in length, e.g. about 33 nucleotides. The second oligonucleotide comprises at least 7 nucleotides, and an exemplary second oligonucleotide comprises about 11 nucleotides.

The invention also includes to an RNA oligonucleotide complex for modulating the expression or activity of a cystic fibrosis transmembrane conductance regulator (CFTR) gene product, the complex comprising a first oligonucleotide and a second oligonucleotide, the first oligonucleotide comprising the nucleic acid sequence of SEQ ID NO:1 and the second oligonucleotide comprising the nucleic acid sequence of SEQ ID NO:2, wherein the first and second oligonucleotide are annealed.

A method for targeted gene repair, is carried out by contacting a target RNA of a cell with a hybrid DNA/RNA oligonucleotide complex, the complex comprising a first strand and a second strand, the first strand comprising a flanking sequence complementary to the target RNA and central sequence comprising at least one non-complementary nucleotide in a location opposite a defect of the target RNA, wherein the flanking sequence of the first strand comprises an RNase H-resistant modification 3' and 5' to the nucleotide, the first strand and the second strand being annealed; and hybridizing the complex to the target RNA, wherein a repaired RNA is produced, the RNA comprising a sequence alteration opposite the defect of the target RNA, wherein the genomic target DNA sequence is unaltered. For example, the first strand and second strand are of equal length. Alternatively, the strand is shorter than the first strand In another embodiment, the methods further comprise contacting the target RNA with a phosphorothioate (PS) containing sequence of a deoxynucleotide with RNase H resistant flanking ends. Following contacting the target RNA with a phosphorothioate (PS) containing sequence, the target RNA is treated with annealed hybrid oligonucleotide complex, and a repaired RNA is produced.

The defect to be repaired is a substitution, deletion, or addition of at least one base pair compared to a normal wild type sequence. The alteration is not maintained in a progeny of the cell.

One type of RNase H-resistant modification is the addition of a 2'-O-methyl moiety. At least one nucleotide of the flanking sequence 3' to the oligonucleotide hybridizable to the target and at least one nucleotide of the flanking sequence 5' to the oligonucleotide hybridizable to the target comprise the RNase H-resistant modification. The first strand comprises an RNase activating oligonucleotide comprising a phosphorothioate linkage flanked by RNase H resistant segments.

Other features and advantages of the invention will be apparent from the following description and from the claims.

BRIEF DESCRIPTIONS OF THE DRAWINGS

FIG. 1 is a set of tracings of whole cell currents of Δ508CFTR expressing cells. FIG. 1, Top Panel shows representative tracings of Δ508CFTR expressing cells after treatment with CF4/CF6 were obtained before and after stimulation with a cAMP mixture. The cAMP-activated currents were inhibited by DPC (500 μM). FIG. 1, Bottom Panel, Left shows that untreated Δ508 cells lacked a cAMP activated whole cell conductance (n=21). FIG. 1, Bottom Panel, Center shows, in contrast, that CF4/CF6 treated Δ508 cells had a robust cAMP response (Linear whole-cell currents were observed before and after cAMP activation). FIG. 1, Bottom Panel, Right shows that cAMP activation in treated cells was inhibited by DPC. Similar results were obtained when the initially used two-step insertion mechanism was employed.

Figure 2A:
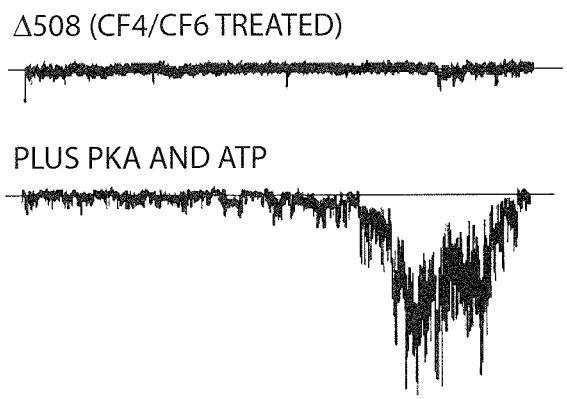
Figure 2B:
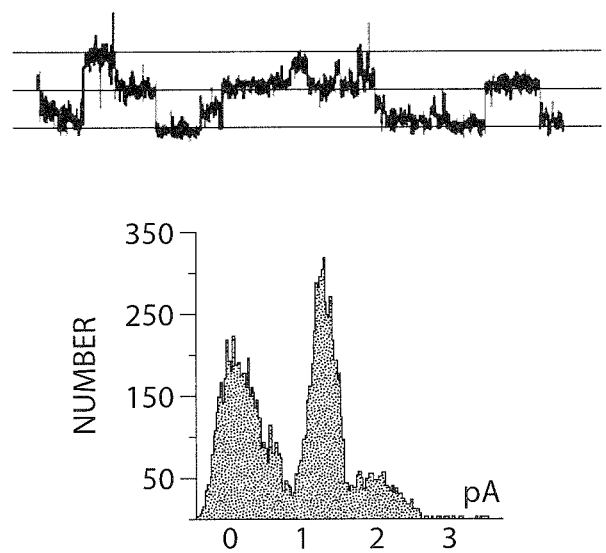

FIG. 2 is a set of tracings of single channel currents of Δ508CFTR expressing cells. FIG. 2A, Top Panel, shows a representative tracing of current observed in Δ508CFTR expressing cells after treatment with CF4/CF6. Currents were obtained in excised inside-out patches. FIG. 2A, Bottom Panel shows that addition of PKA (100 nM) and MgATP (1 mM) induced rapid channel activation. Data are representative of n=12 experiments. No activation was observed in control Δ508CFTR expressing cells. FIG. 2B, Top Panel, shows that the PKA-activated Cl$^-$ single channel currents had a single channel conductance of 12 pS (n=6). FIG. 2B, Bottom Panel, the all-point histograms show the details of Cl$^-$ single channel conductance.

Figure 3:
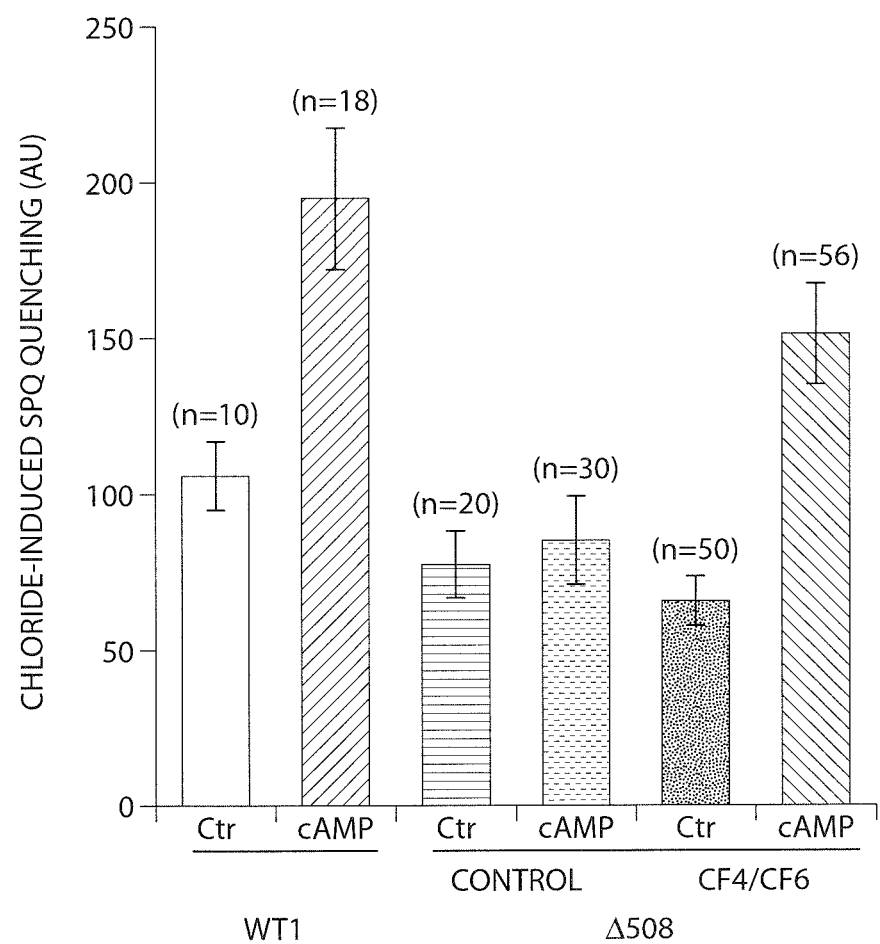

FIG. 3 is a set of bar graphs that show the results of an SPQ fluorescence assay. Cl$^-$ induced changes in fluorescence were followed in cells loaded with the Cl$^-$ sensitive dye SPQ. SPQ fluorescence was tested in WT1 cells expressing wild type CFTR, and control and treated Δ508 cells in a custom-made chamber, under UV-fluorescence microscopy. A cAMP-induced response (5-15 min) was only observed in WT1 and treated Δ508 cells (p<0.05). Numbers in parentheses indicate individual cells analyzed.

Figure 4:
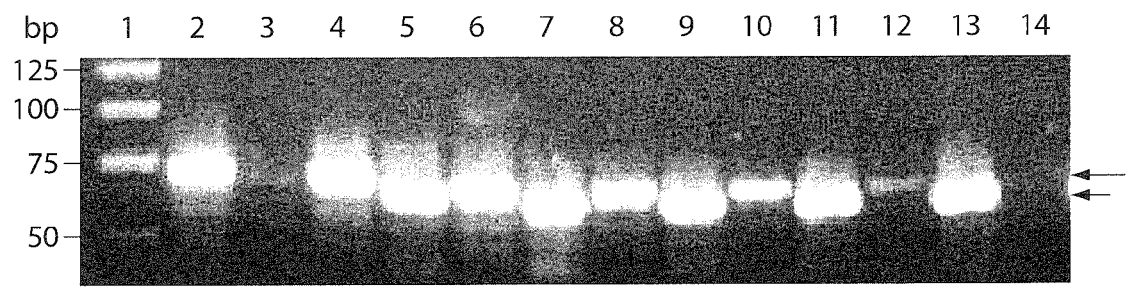

FIG. 4 is a photograph of an agarose gel electrophoretogram showing allele-specific RT-PCR analysis of CFTR mRNA. Samples from WT1 mRNA were diluted into Δ508 mRNA (lanes 2 to 14, from undiluted to $10^6$ order with 10-fold serial dilutions) to test efficiency of allele-specific primers (CFFW and CFFM, Table 1). Lanes 2 and 3 show WT1 and Δ508 mRNA amplified with respective primers. The wild type primers recognized WT1 mRNA in dilutions of up to $1:10^5$ (Lanes 11 and 12). Gel electrophoresis was conducted in agarose gels (3%), and a 25 base pair (bp) ladder is shown on the left lane.

Figure 5:
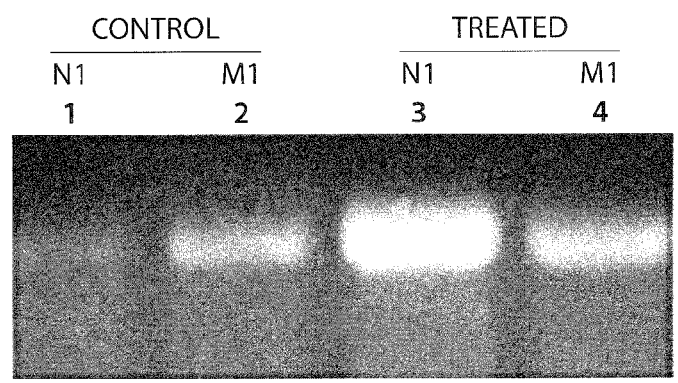

FIG. 5 is a photograph of an agarose gel electrophoretogram showing specific reverse primer analysis of mRNA in samples of RT-PCR material obtained by amplification with wild type (N1) and mutant (M1) specific reverse primers (Table 1). Lanes 1 and 2 are Δ508 untreated and RT PCR with N1 and M1 primers respectively. Similarly lanes 3 and 4 are Δ508 treated with CF4/CF6 and following RT PCR with N1 and M1 primers respectively. Gel electrophoresis was performed in 3% agarose gel.

Figure 6:
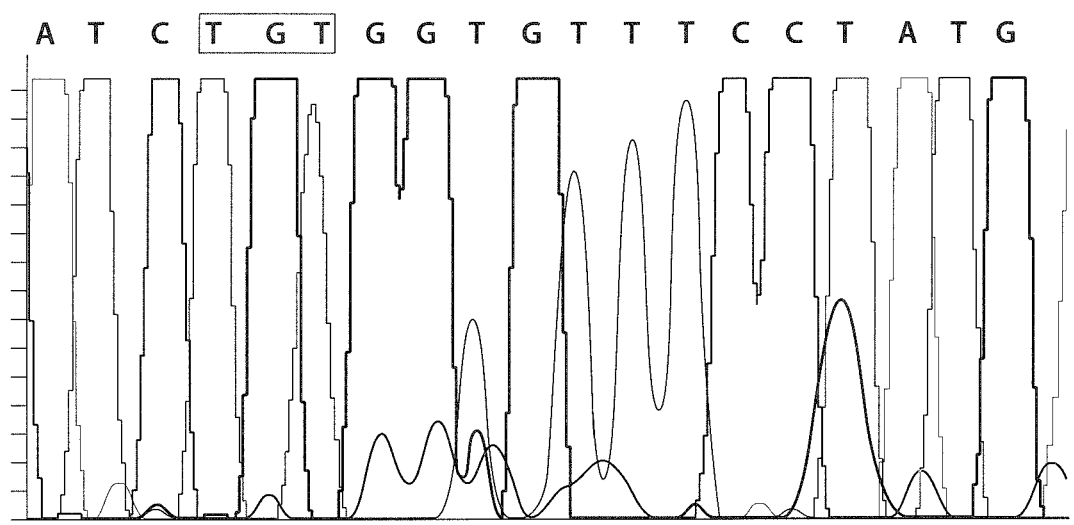

FIG. 6 is an automated tracing by type of nucleotide base obtained from DNA sequencing of RT-PCR products (SEQ ID NO: 20). Sequence analysis of the CF4/CF6 treated Δ508CFTR was conducted by RT-PCR analysis of total RNA. The PCR materials observed in the gel were subcloned in pCR-Blunt vector and sequenced at the MGH Sequencing Facility. Minor peaks represent background. Variations in heights of peaks are due to instrumental sensitivity Scheme 1 is a drawing of (A) a hypothetical scheme for repair of CFTR Δ508 mRNA by CF4/CF6 duplex (SEQ ID NO: 21 corresponding to the Wild Type sequence, SEQ ID NO: 22 corresponding to the Δ508 mRNA sequence, SEQ ID NO: 1 corresponding to the CF4 sequence, and SEQ ID NO: 2 corresponding to the CF6 sequence), and (B) sequences found in restored mRNA (SEQ ID NO: 58 corresponding to the N1 sequence, SEQ ID NO: 59 corresponding to the NF1 sequence, SEQ ID NO: 60, corresponding to the SNF1 sequence). Bold italic type corresponds to bases of 2'-O-methyl ribosyl oligonucleotides with normal internucleoside phosphate bonds (CF4 oligonucleotide). Regular type corresponds to natural RNA. Bold plus underlined type corresponds to inserted bases of ribonucleotides. Shaded bases in the CF4 and Δ508 mRNA indicate non-complementary Watson-Crick base pairs. Sequence analysis of RT-PCR products obtained by using different primers is also shown. (a) A in square indicates that in 7 out of 10 sequencing this A was present, but in 3 other sequencings was absent, leaving 3 deletions. (b) Dashes indicate deletions, possibly induced by PCR. (c) There are no deletions. U in square indicates that in this position U sometimes is replaced by another nucleotide.

Figure 8:
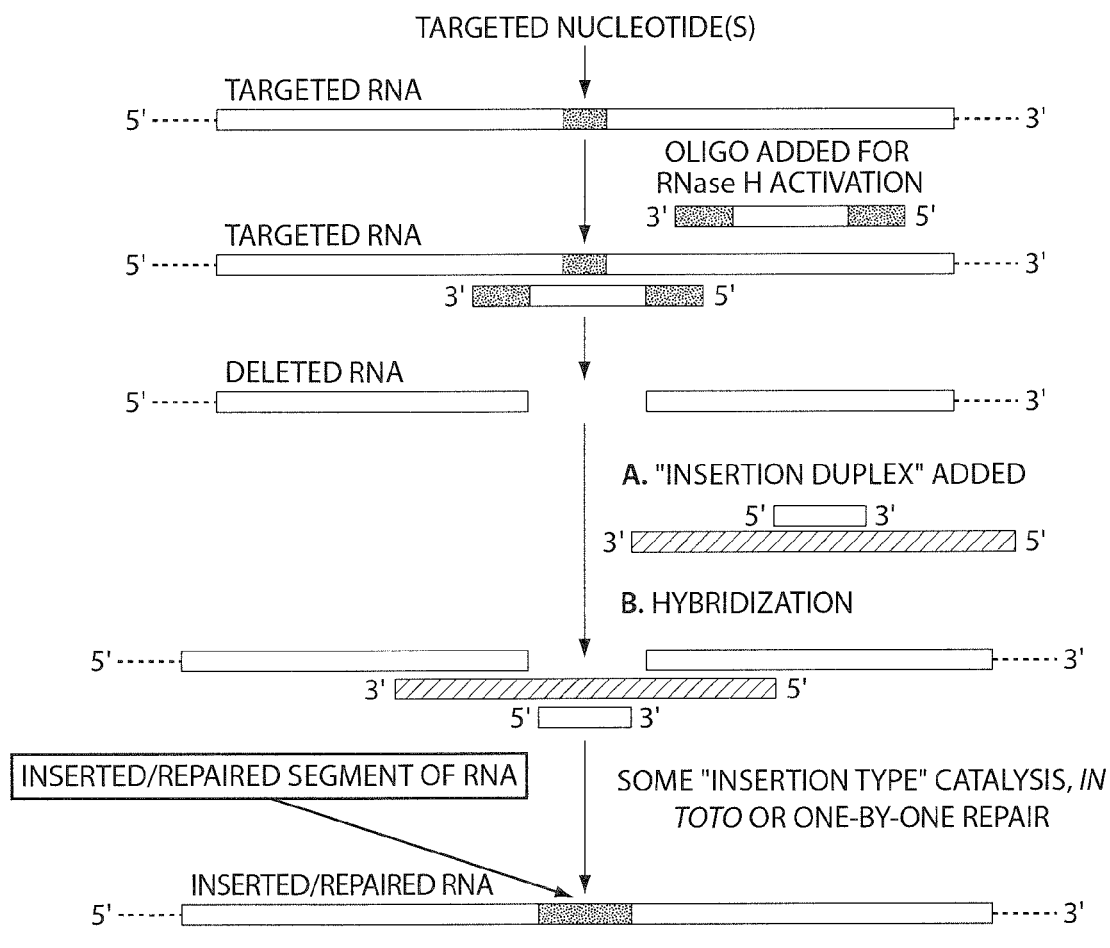
Figure 9:
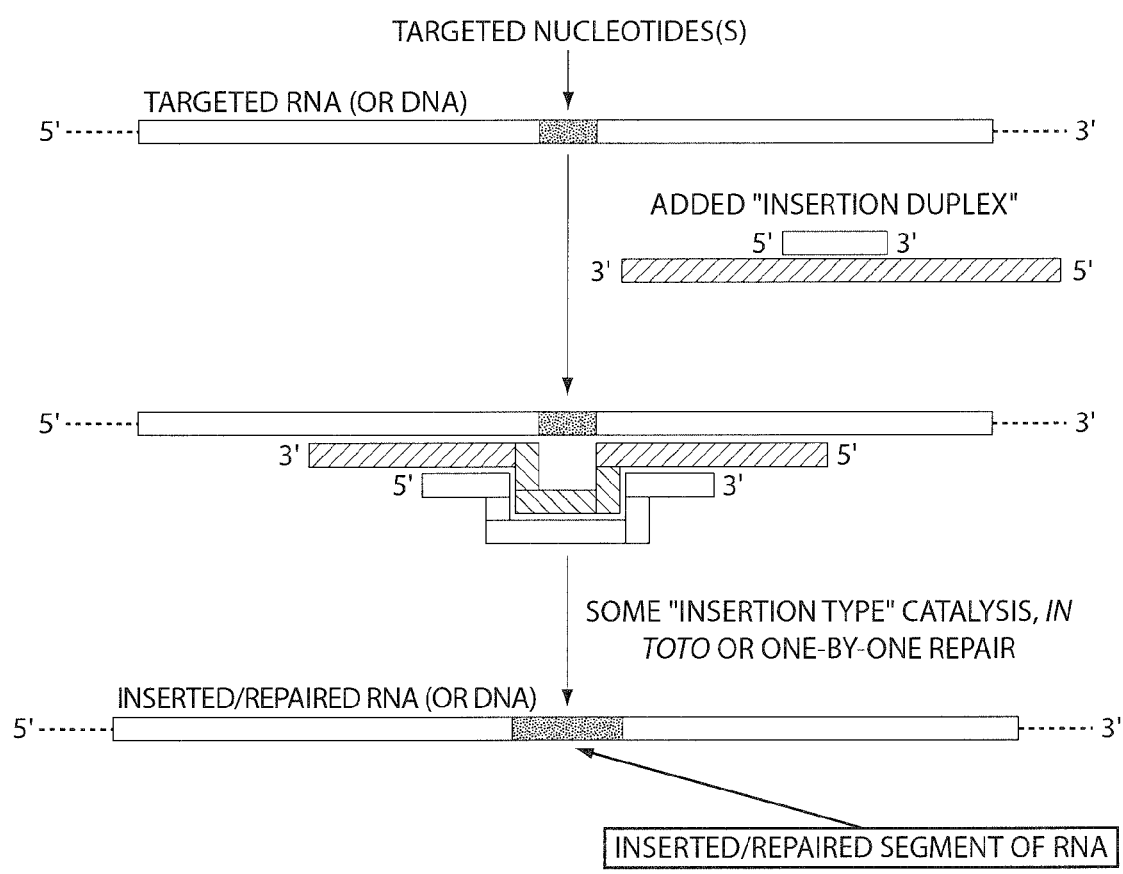
Figure 10:
Figure 11:
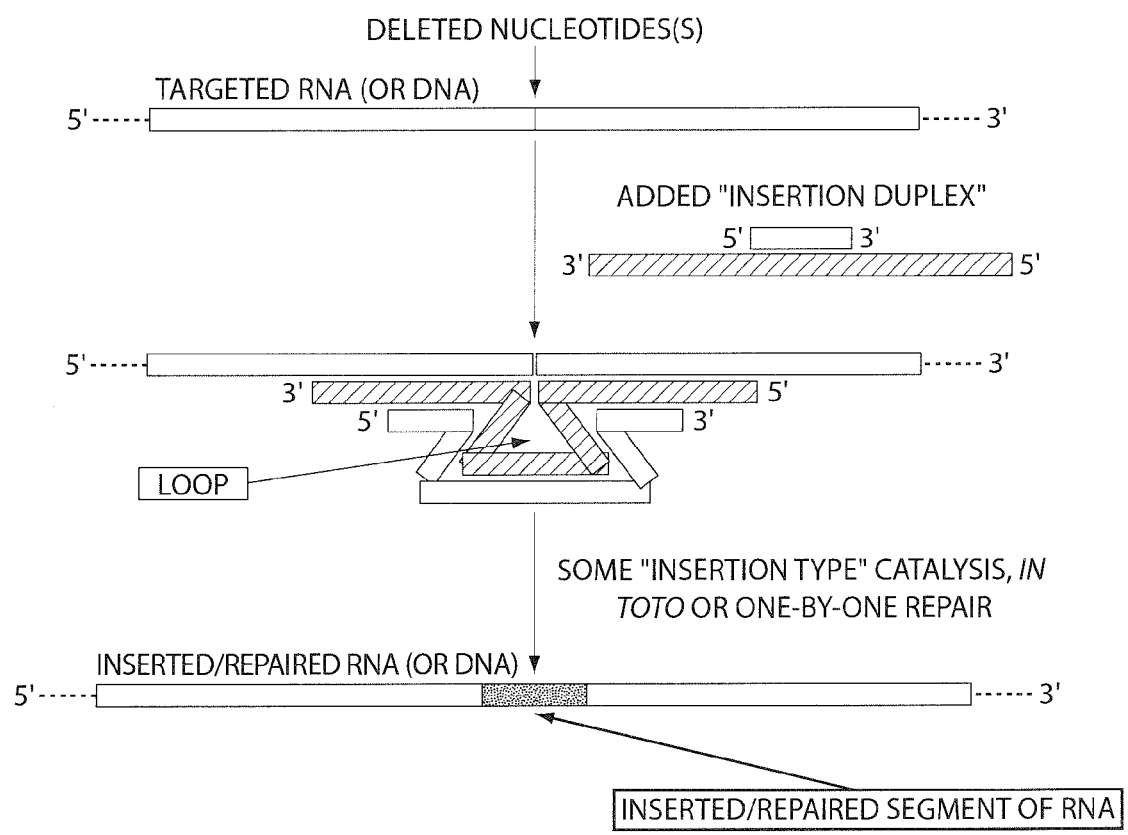

FIG. 8 shows scheme 2. Scheme 2 is a drawing of a hypothetical site-specific deletion/insertion mechanism in the RNA containing mismatch region, with the two-step nucleotide complex technique. Red corresponds to targeted nucleotide(s), black and white correspond to hybrid oligonucleotide for RNase-H activation, yellow corresponds to natural RNA, grey corresponds to template oligonucleotide in insertion/deletion duplex, and blue corresponds to inserted/repaired segment of RNA FIG. 9 shows scheme 3. Scheme 3 is a drawing of a hypothetical site-specific deletion/insertion mechanism in the RNA containing mismatch region, with the one step oligonucleotide complex technique. Red corresponds to targeted nucleotide(s), yellow corresponds to natural RNA, grey corresponds to template oligonucleotide in insertion/deletion duplex, and blue corresponds to inserted/repaired segment of RNA FIG. 10 shows scheme 4. Scheme 4 is a drawing of a hypothetical site-specific deletion/insertion mechanism in the RNA containing deleted region, with the two-step oligonucleotide complex technique. Black and white correspond to hybrid oligonucleotide for RNase-H activation, yellow corresponds to natural RNA, grey corresponds to template oligonucleotide in insertion/deletion duplex, and blue corresponds to inserted/repaired segment of RNA FIG. 11 shows scheme 5. Scheme 5 is a drawing of a hypothetical site-specific insertion/deletion mechanism in the RNA containing deleted region, with the one step oligonucleotide complex technique. Yellow corresponds to natural RNA, grey corresponds to template oligonucleotide in "insertion duplex", and blue corresponds to inserted/repaired segment of RNA (or DNA).

Figure 12:
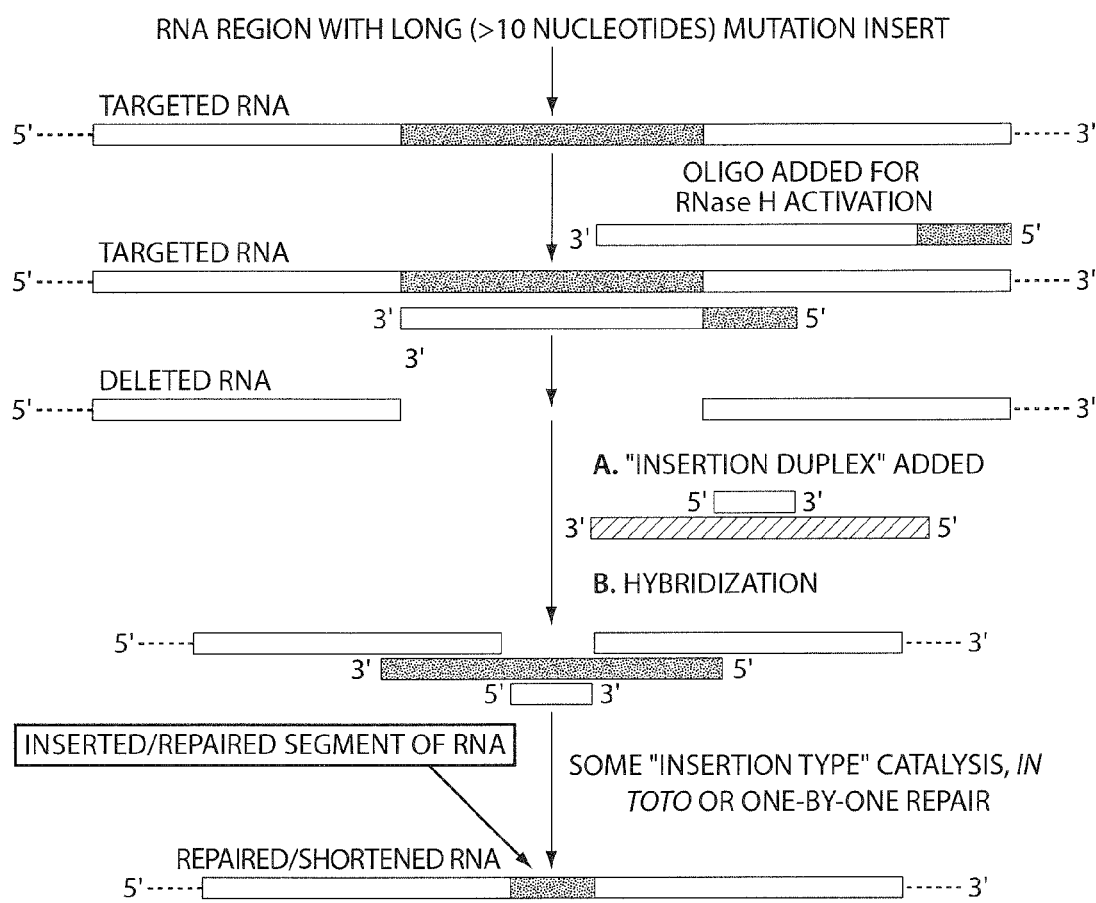
Figure 13:
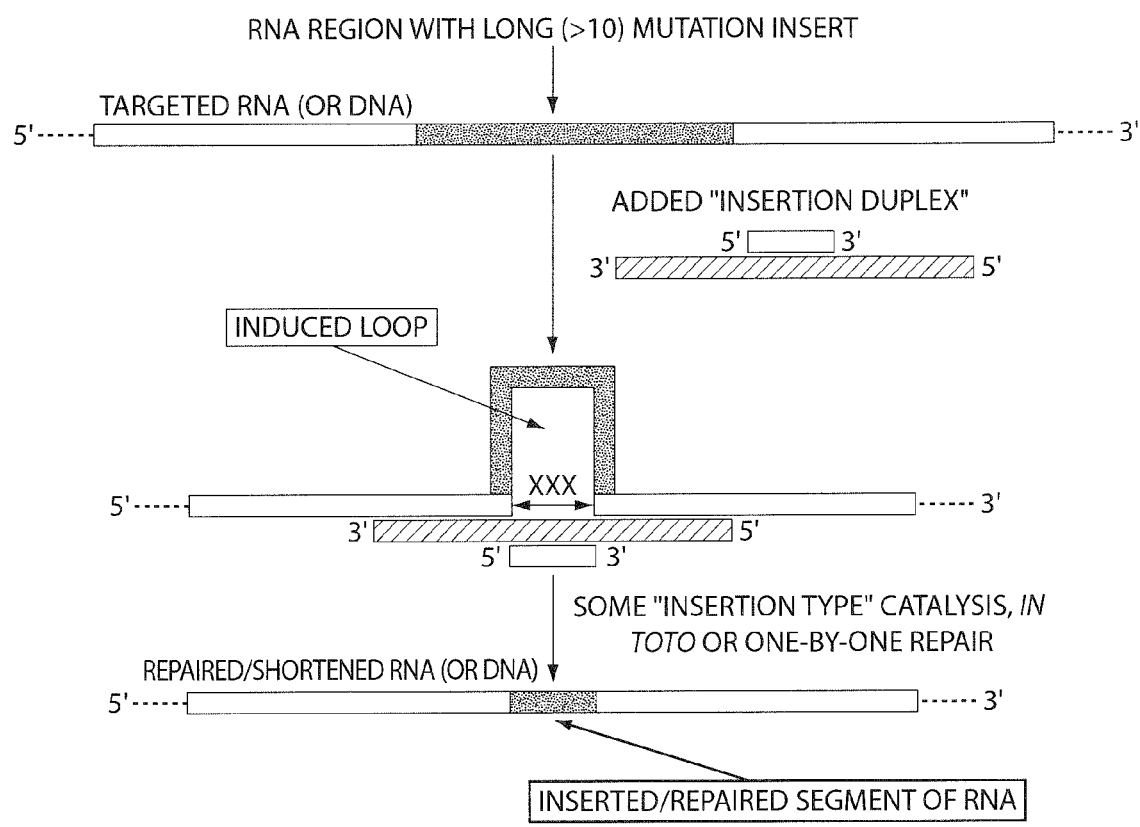

FIG. 12 shows scheme 6. Scheme 6 is a drawing of a hypothetical site-specific deletion/insertion mechanism in the RNA containing repeat mutations, with the two-step oligonucleotide complex technique. Red corresponds to targeted nucleotide(s), black and white correspond to hybrid oligonucleotide for RNase-H activation, yellow corresponds to natural RNA, grey corresponds to template oligonucleotide in insertion/deletion duplex, and blue corresponds to inserted/repaired segment of RNA FIG. 13 shows scheme 7. Scheme 7 is a drawing of a hypothetical site-specific deletion/insertion mechanism in the RNA containing repeat mutations, with the one step oligonucleotide complex technique. Red corresponds to targeted nucleotide(s), yellow corresponds to natural RNA, grey corresponds to template oligonucleotide in insertion/ deletion duplex, and blue corresponds to inserted/repaired segment of RNA. The XXX indicates the size of the base of the oligonucleotide loop. It may vary between zero and twenty.

Figure 14:
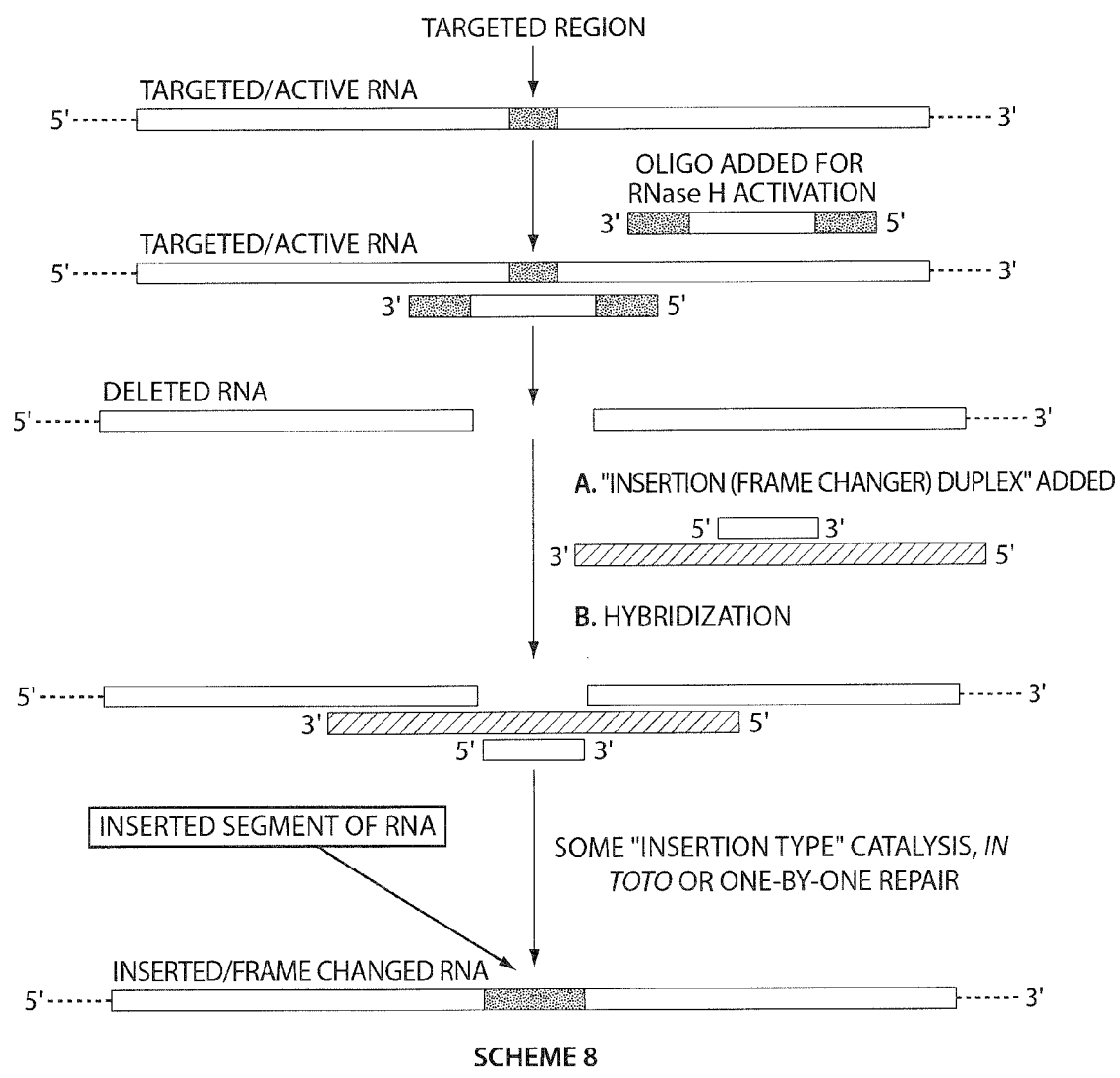
Figure 15:
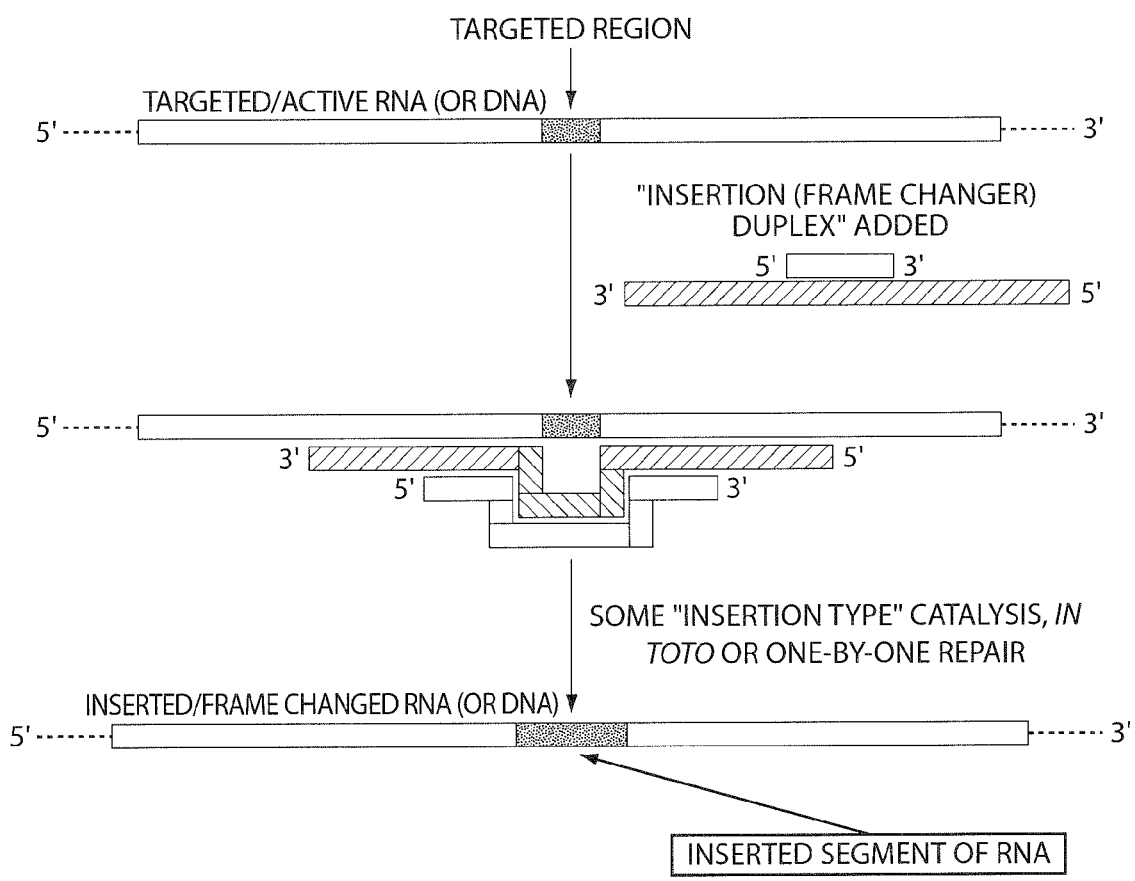

FIG. 14 shows scheme 8. Scheme 8 is a drawing of a hypothetical site-specific frame changing mechanism in the active RNA, with the two-step oligonucleotide complex technique. Red corresponds to targeted nucleotide(s), black and white correspond to hybrid oligonucleotide for RNase-H activation, yellow corresponds to natural RNA, grey corresponds to template oligonucleotide in insertion/deletion duplex, and blue corresponds to inserted/frame changed segment of RNA FIG. 15 shows scheme 9. Scheme 9 is a drawing of a hypothetical site-specific frame changing mechanism in the active RNA, with the one step oligonucleotide complex technique. Red corresponds to targeted nucleotide(s), yellow corresponds to natural RNA, grey corresponds to template oligonucleotide in insertion/deletion duplex, and blue corresponds to inserted/frame changed segment of RNA.

Figure 16:
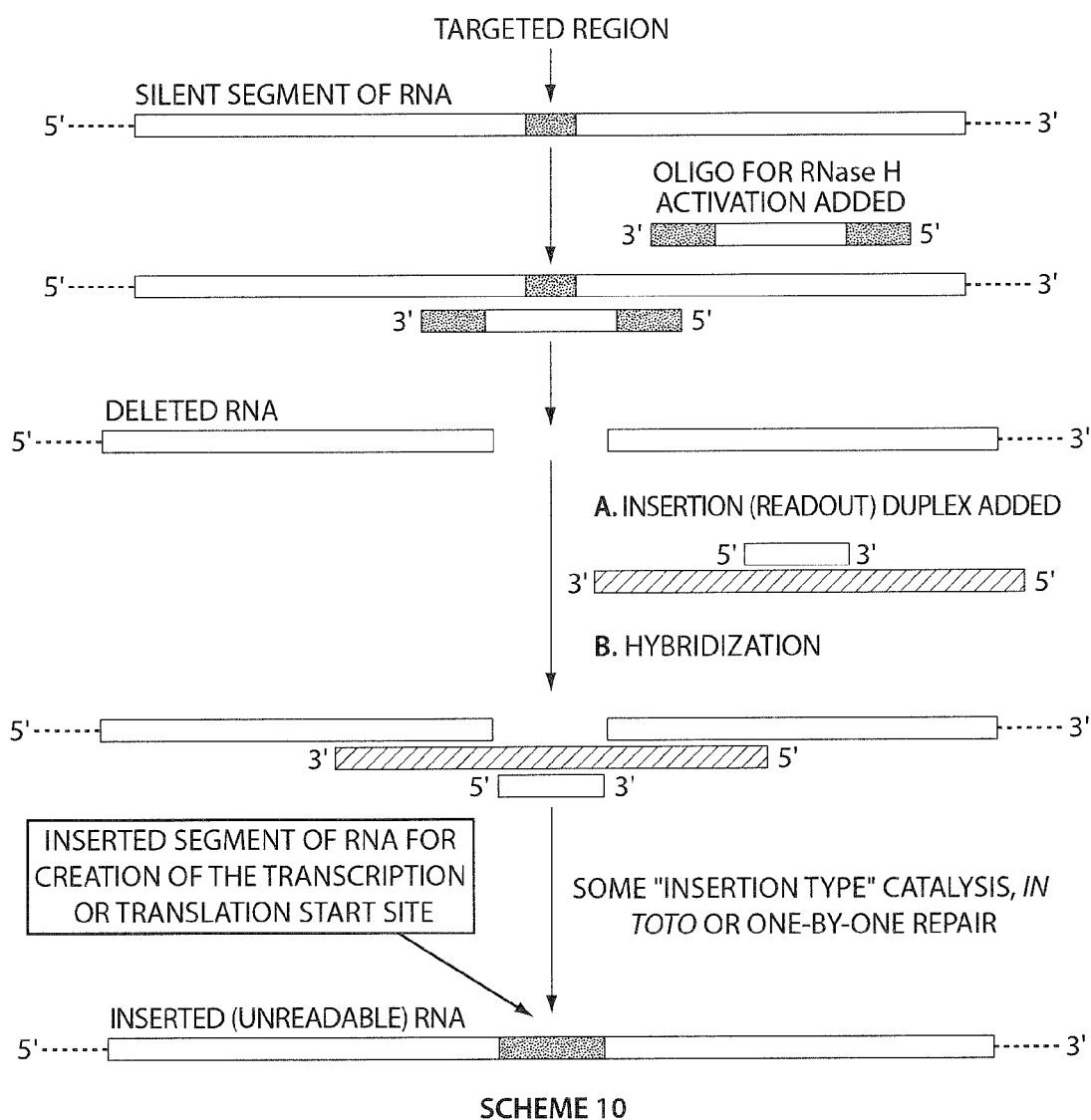

FIG. 16 shows scheme 10. Scheme 10 is a drawing of a hypothetical site-specific transcription or translation start site insertion mechanism in the active RNA, with the two-step oligonucleotide complex technique. Red corresponds to targeted nucleotide(s), black and white correspond to hybrid oligonucleotide for RNase-H activation, yellow corresponds to natural RNA, grey corresponds to template oligonucleotide in insertion/deletion duplex, and blue corresponds to inserted/frame changed segment of RNA.

Figure 17:
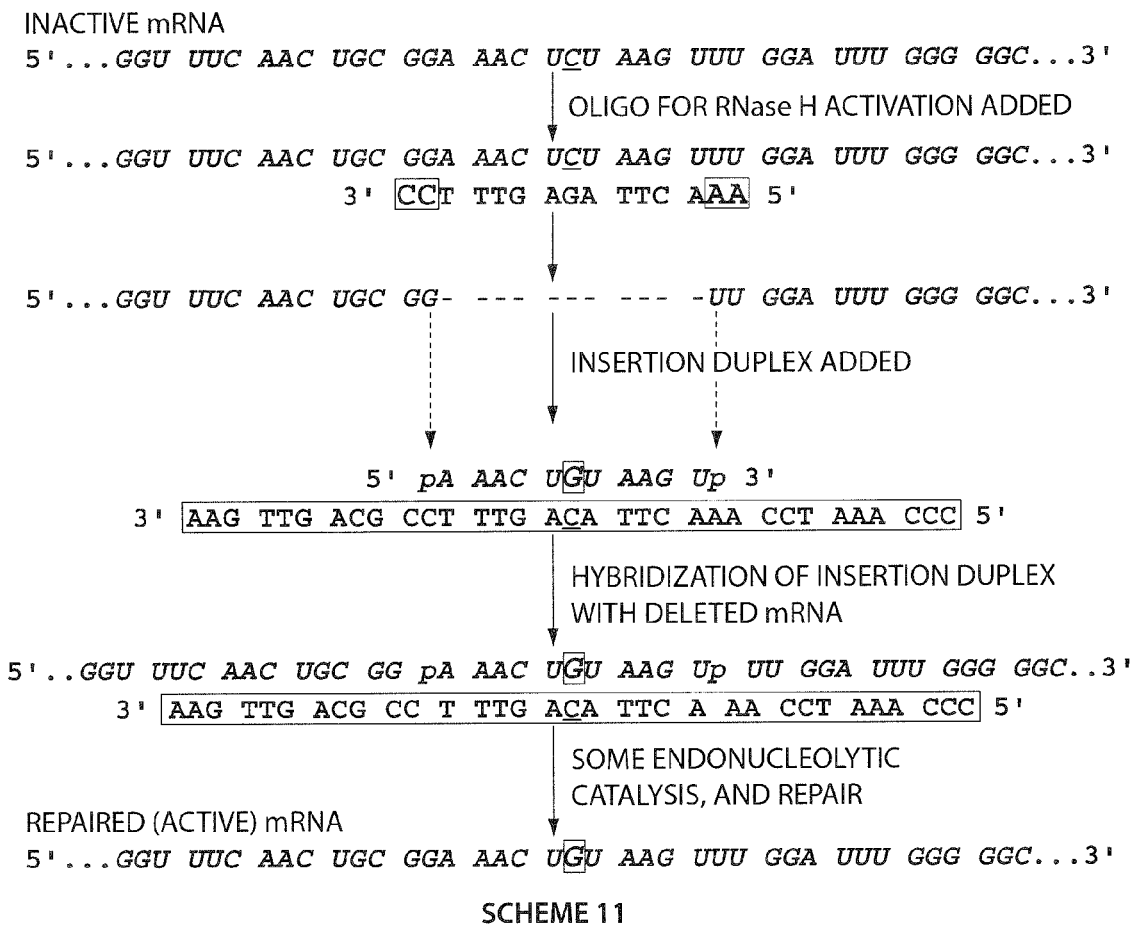

FIG. 17 shows scheme 11. Scheme 11 is a drawing of a hypothetical scheme for repair of inactive tyrosinase by two-step oligonucleotide complex technique (depicting SEQ ID NO: 23, SEQ ID NO: 23, SEQ ID NO: 24, SEQ ID NO:

25 (left side schematic sequence), SEQ ID NO: 26 (right side schematic sequence), SEQ ID NO: 27, SEQ ID NO: 28, SEQ ID NO: 29, SEQ ID NO: 30, and SEQ ID NO: 31, from top to bottom, respectively). Bold italic type corresponds to natural RNA. Small caps correspond to PS ODN. Shaded corresponds to 2'-O-methylribosyl oligonucleotides, with internucleoside phosphate bonds. Underline base corresponds to targeted base. Base in square box corresponds to replaced base.

Figure 18:
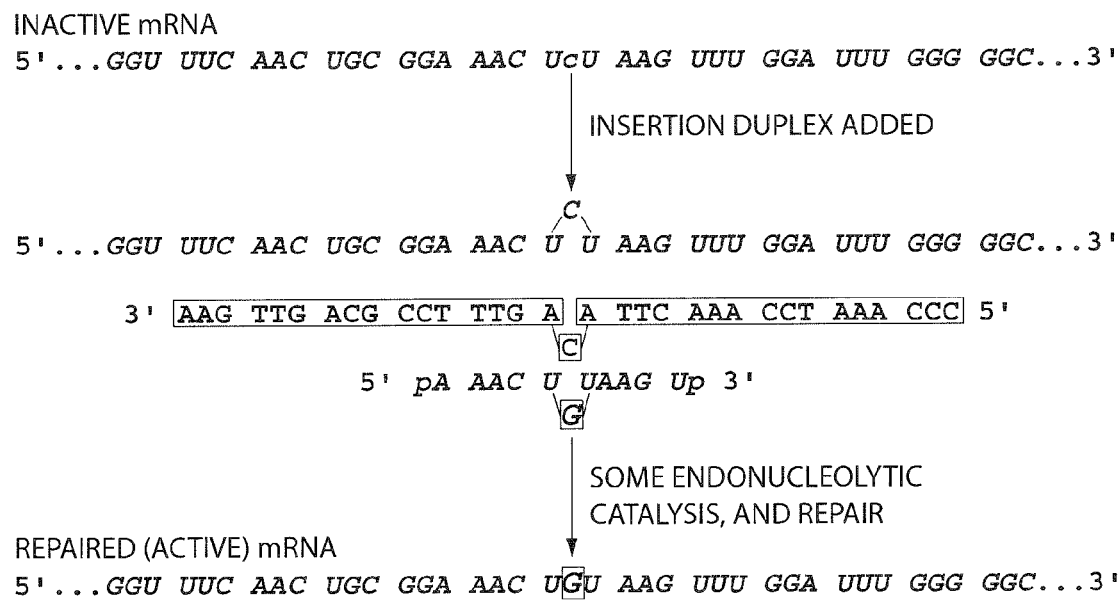

FIG. 18 shows scheme 12. Scheme 12 is a drawing of a hypothetical scheme for repair of inactive tyrosinase by one-step oligonucleotide complex technique (depicting SEQ ID NO: 32, SEQ ID NO: 32, SEQ ID NO: 33, SEQ ID NO: 34, and SEQ ID NO: 35, from top to bottom, respectively). Bold italic type corresponds to natural RNA. Small caps correspond to thiophosphate oligodeoxynucleotide. Shaded corresponds to 2'-O-methylribosyl oligonucleotides, with internucleoside phosphate bonds. Underline base corresponds to targeted base. Base in squire square box corresponds to replaced base.

Figure 19:
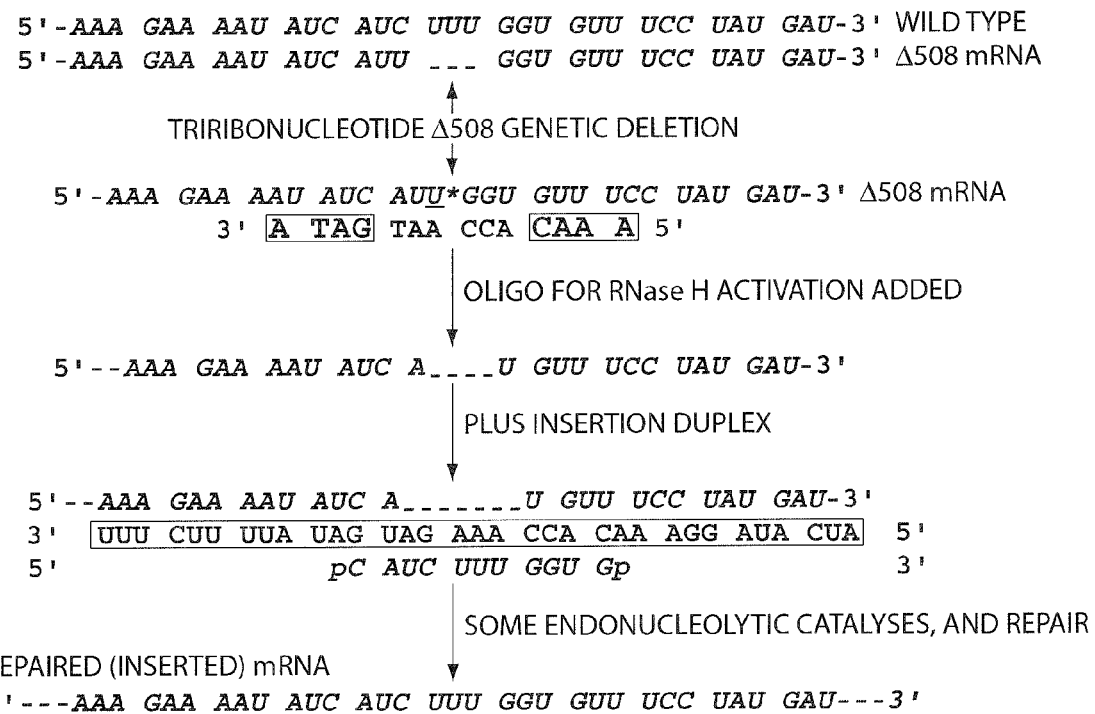

FIG. 19 shows scheme 13. Scheme 13 is a drawing of a hypothetical scheme for repair of Cystic Fibrosis Δ508 mRNA by two-step oligonucleotide complex technique (depicting SEQ ID NO: 21, SEQ ID NO: 22, SEQ ID NO: 22, SEQ ID NO: 36, SEQ ID NO: 37, SEQ ID NO: 37, SEQ ID NO: 38, SEQ ID NO:39, and SEQ ID NO: 40, from top to bottom, respectively). Bold italic type corresponds to natural RNA. Small caps correspond to thiophosphate oligodeoxynucleotyde. Shaded corresponds to 2'-O-methylribosyl oligonucleotides, with internucleoside phosphate bonds. * and - - - corresponds to deletion region of mutated mRNA.

Figure 20:
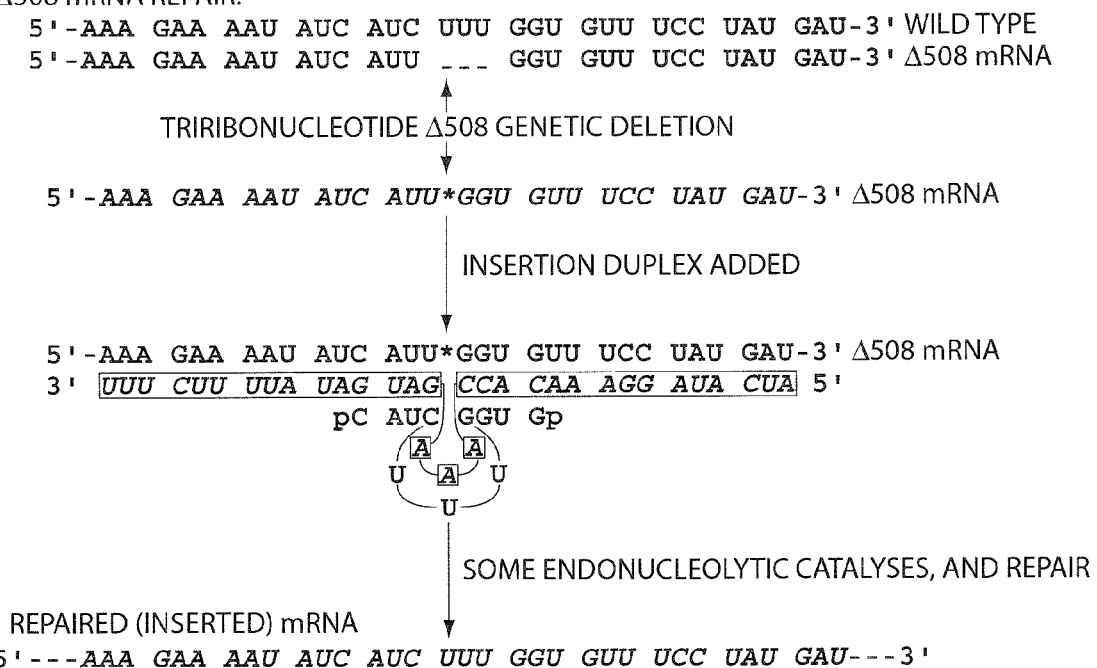

FIG. 20 shows scheme 14. Scheme 14 is a drawing of a hypothetical scheme for repair of Cystic Fibrosis Δ508 mRNA by one step oligonucleotide complex technique (depicting SEQ ID NO: 21, SEQ ID NO: 22, SEQ ID NO: 22, SEQ ID NO: 22, SEQ ID NO: 41, SEQ ID NO: 39, and SEQ ID NO: 42, from top to bottom, respectively). Bold italic type corresponds to natural RNA. Shaded corresponds to 2'-O-methylribosyl oligonucleotides, with internucleoside phosphate bonds. * and - - - correspond to a deletion region of mutated mRNA.

FIG. 21 shows scheme 15. Scheme 15 shows the insertion into the gene for Huntingtin protein with HT3 followed by HT4/HT6 duplex oligonucleotides (depicting SEQ ID NO: 43, SEQ ID NO: 44, SEQ ID NO: 43, SEQ ID NO: 14, SEQ ID NO: 45 (left of cut mRNA), SEQ ID NO: 46 (right of cut mRNA), SEQ ID NO: 15, SEQ ID NO: 16, SEQ ID NO: 47, SEQ ID NO: 48, and SEQ ID NO: 49, from top to bottom, respectively). Shaded type in sequences correspond to bases of 2'-O-methylribosyl oligonucleotides, with internucleoside phosphate bonds. Regular type corresponds to natural RNA. Bold type in square corresponds to the inserted segment of mRNA. There is purposely deleted one base (x) in modified mRNA. Lower case p corresponds to terminal phosphate groups.

FIG. 22 shows scheme 16. Scheme 16 shows the insertion into the Aim-1 gene with Alb3 followed by Alb4/Alb6 duplex oligonucleotides. Shaded type in sequences corresponds to bases of 2'-O-methylribosyl oligonucleotides, with internucleoside phosphate bonds. Regular type corresponds to natural RNA. Strikethrough in the sequence of repaired mRNA corresponds to inserted segment of mRNA. Lower case p corresponds to terminal phosphate groups.

DETAILED DESCRIPTION

The present invention is directed to a method for targeted gene repair, comprising contacting a non-repaired target RNA with an RNA oligonucleotide complex comprising a first oligonucleotide and a second oligonucleotide, the first oligonucleotide comprising a sequence complementary to a repaired target RNA, wherein the RNA sequence of the first oligonucleotide comprises an RNase H-resistant modification, and the second oligonucleotide comprises an RNA sequence complementary to at least 6 nucleotides of the first oligonucleotide at the site on the sequence of the first oligonucleotide which is not complementary to the non-repaired target RNA; and hybridizing the complex to the non-repaired target RNA in the presence of an RNase, wherein a repaired RNA is produced. Preferably, any genetic defect, e.g., a substitution, deletion, or addition of at least one basepair, compared to a normal wild type sequence, is phenotypically changed.

The first oligonucleotide and the second oligonucleotide are annealed. The repaired target RNA is an optionally wild-type sequence, and the non-repaired target RNA is a mutated sequence. The mutation is a substitution, deletion or insertion of at least one base pair compared to a normal wild type sequence. In one embodiment, prior to contacting a non-repaired target RNA with an RNA oligonucleotide complex the non-repaired target RNA is contacted with a phosphorothioate (PS) containing sequence comprising a deoxynucleotide with RNase H resistant flanking ends. The RNase H-resistant modification is the addition of a 2'-O-methyl moiety. The first oligonucleotide is at least 10 nucleotides in length. In a preferred embodiment, the first oligonucleotide comprises about 33 nucleotides. In another embodiment, the second oligonucleotide comprises at least 7 nucleotides. In a preferred embodiment, the second oligonucleotide comprises about 11 nucleotides. Contacting the target RNA occurs within a cell. In preferred embodiment, cell is in vitro, ex vivo or in vivo. In another preferred embodiment, the cell is a mammalian cell. In a more preferred embodiment, the cell is a human cell.

The present invention is also directed to a method for treating or ameliorating cystic fibrosis in a subject in need thereof, comprising administering an RNA oligonucleotide complex directed to a non-repaired target RNA, the complex comprising a first oligonucleotide and a second oligonucleotide, the first oligonucleotide comprising a sequence complementary to a repaired target RNA, wherein the RNA sequence of the first oligonucleotide comprises an RNase H-resistant modification, and the second oligonucleotide comprises an RNA sequence complementary to at least 6 nucleotides of the first oligonucleotide at the site on the sequence of the first oligonucleotide which is not complementary to the non-repaired target RNA; and wherein administration produces a repaired targeted RNA, thereby treating or ameliorating cystic fibrosis.

The first oligonucleotide and the second oligonucleotide are annealed.

The repaired target RNA is a wild-type sequence. In another embodiment, the non-repaired target RNA is a mutated sequence. In a preferred embodiment, mutation is a substitution, deletion or insertion of at least one base pair compared to a normal wild type sequence.

Prior to administering an RNA oligonucleotide complex, a phosphorothioate (PS) containing sequence comprising a deoxynucleotide with RNase H resistant flanking ends is administered. RNase H-resistant modification is the addition of a 2'-O-methyl moiety. The first oligonucleotide is at least 10 nucleotides in length. In a preferred embodiment, the first oligonucleotide comprises about 33 nucleotides. In another embodiment, the second oligonucleotide comprises at least 7 nucleotides. In a preferred embodiment, the second oligonucleotide comprises about 11 nucleotides.

The present invention is also directed to an RNA oligonucleotide complex for modulating the expression or activity of a disease-associate gene product cystic fibrosis transmembrane conductance regulator (CFTR) gene product, the complex comprising a first oligonucleotide and a second oligonucleotide, the first oligonucleotide comprising the nucleic acid sequence of SEQ ID NO:1 and the second oligonucleotide comprising the nucleic acid sequence of SEQ ID NO:2, wherein the first and second oligonucleotide are annealed.

The present invention includes method for targeted gene repair, comprising contacting a target RNA of a cell with a hybrid DNA/RNA oligonucleotide complex, the complex comprising a first strand and a second strand, the first strand comprising a flanking sequence complementary to the target RNA and central sequence comprising at least one non-complementary nucleotide in a location opposite a defect of the target RNA, wherein the flanking sequence of the first strand comprises an RNase H-resistant modification 3' and 5' to the nucleotide, the first strand and the second strand being annealed; and hybridizing the complex to the target RNA, wherein a repaired RNA is produced, the RNA comprising a sequence alteration opposite the defect of the target RNA, wherein the genomic target DNA sequence is unaltered.

The complex contains a first strand and a second strand. The first and second strand is annealed to one another to form the complex. The first strand contains a flanking sequence that is complementary to sequence of the target RNA ("hybridized ends") and a central sequence (located between the flanking sequence) that contains at least one non-complementary nucleotide or deletion in a location opposite a defect of the target RNA. The nucleotide sequence of the first strand is complementary to the sequence of a normal wild type gene. The central sequence, which is RNase-sensitive, is at least a triplet, and is preferably at least 4, 5, 6, or more nucleotides in length. The flanking sequence of the first strand includes an RNase H-resistant modification, e.g., addition of a 2'-O-methyl moiety, or other modifications, to both a 3' and 5' to the nucleotide hybridizable to the target sequence of the gene.

The second strand of the complex is of the same length as the first strand, or is shorter than first strand of the complex, and the second and first strands are complementary to and annealed to one another. The complex is allowed to hybridize to target genomic RNA of the target cell, and a repaired RNA is produced in the cell. The repaired RNA contains a sequence alteration opposite the defect of the target RNA, and the genomic target DNA sequence remains unaltered. The RNA alteration or phenotypic change accomplished by the method is not maintained in a progeny of the cell, i.e., is not heritable.

The flanking sequence of the first strand contains at least four complementary nucleotides (relative to the genomic target RNA) 3' to the hybridizable sequence of the targeted gene (of the target RNA and first strand RNA oligonucletide) and at least four complementary nucleotides (relative to the genomic target RNA) 5' to the hybridizable sequence of the targeted gene. The flanking portion of the complex sequence contains an RNase H-resistant modification, whereas the central portion of the sequence (opposite the defect) does not contain such a modification and is therefore nuclease and RNase sensitive, i.e., the nucleotide bonds in the central region are enzymatically cleaved.

The first strand is at least 10 nucleotides in length. For example, the first strand contains at least about 10, 12, 14, 15, 16, 18, 20, 30, 40, or 50 or more nucleotides, the flanking sequence of which contains at least 2 nucleotides that are complementary to target RNA in the region of the defect. The complementary flanking sequence on either side of the defect is about 5, 10, 15, 20, 25 or more nucleotides in length. The second strand of the oligonucleotide complex is at least about 7 nucleotides in length and is optionally longer, e.g., 9, 11, 12, 15, or 20 nucleotides.

Another approach involves hybridization of a PS containing segment of a deoxyribonucleotide with RNase H resistant flanking ends, resulting in an RNase-catalyzed deletion of a small central segment of mRNA. This oligonucleotide is then washed out of the incubation medium and is replaced by a double-stranded, annealed hybrid oligonucleotide. The double-stranded, annealed hybrid oligonucleotide hybridizes with the targeted mRNA, and inserts an oligonucleotide segment complementary to the hybridizable oligonucleotide part of the duplex repair complex.

Nucleotide modifications are selected from the group 2'-O-methyl ribosyl; phosphorothioate; peptide nucleic acid; 2'-halo, 2'-fluoro, 2'-alkyl, 2'-alkoxylalkyl, bridged sugars and similar chemical moieties; methylphosphonate, ethylphosphonate, phosphoramidate, thiophosphate, dithiophosphate, morpholino, boronophosphate, morpholinophosphate internucleoside linkages and similar chemical moieties; derivatized heterocycles, and sugars.

The method is utilized in analytical research applications as well as in preventative, diagnostic and therapeutic applications. Complexes are administered to a subject, e.g., a human patient, suffering from a disorder associated with a genetic defect, or to a cell obtained from a patient having a genetic disease. Cells or tissue are contacted in vitro, in vivo or ex vivo. In some embodiments, the cell is an isolated cell in a culture. The method can further involve isolating and sequencing RNA from a contacted cell having a different phenotype from cells from the patient or the culture, wherein altering expression of the target gene is altering an RNA nucleotide sequence.

A target gene such as one associated with a disease state is diagnosed by detecting a mutation compared to the sequence of a normal wild type gene. The central segment of the oligonucleotide repair complex has a normal sequence compared to the target gene. A modification confers ribonuclease resistance. Alternatively, a modification confers induction of ribonuclease activity in the cell. At least one nucleotide of the complex is a 2'-O-methyl ribosyl nucleotide. For example, there is a plurality of 2'-O-methyl ribosyl nucleotides. The second strand can further contain a small chemical group at a 5' or 3' terminus, or the second strand further contains a small chemical group at both 5' and 3' termini. The modification can be located at a nucleotide in a 3' or a 5' terminus, or both. The second strand further comprises a modification comprising a small chemical group in a 3' or a 5' terminus. For example, the small chemical group is selected from phosphate, diphosphate, triphosphate, thiophosphate, dithiophosphate, aldehyde, carboxy, dihydroxy, hydroxyl, methyl, ethyl, sulfhdryl, sulfate, and boronate. The central segment comprises at least one modification, which is a phosphorothioate.

The genetic disease is selected from the group of albinism, cystic fibrosis, muscular dystrophy, myotonic dystrophy, muscular atrophy, sickle cell anemia, hepatic disorder, hemophilia, Crigler-Najjar syndrome, renal tubular acidosis, β-thalassemia, atherosclerosis, Huntington's disease, spinocerebellar ataxia, Machado-Joseph disease, Fragile X, Frederich's ataxia, adenosine deaminase deficiency, hepatocellular carcinoma, hepatoblastoma, osteosarcoma, adenocarcinoma, breast cancer, adrenocortical carcinoma, non-Hodgkin lymphoma, glioblastoma, rhabdomyosarcoma, glioma, sickle cell anemia, haemolytic anaemia, retinoblastoma, ovarian cancer, cystic fibrosis, congential absence of vas deferens, melanoma, adenomatous polyposis, colorectal cancer, factor V deficiency, thrombosis, haemophilia A, haemophilia B, warfarin sensitivity, thalassaemia alpha, haemoglobin variant, haemoglobin H disease, non-polyposis colorectal cancer, endometrial cancer, early onset colorectal cancer, apolipoprotein E, hypercholesterolaemia, Gilbert syndrome, Alzheimer's disease and Schizophrenia.

The methods and compositions of the present invention are used to treat or ameliorate cystic fibrosis, Huntington's disease or albinism. More specifically, methods and compositions of the present invention are used to treat or ameliorate at least one symptom of cystic fibrosis, Huntington's disease or albinism.

Cystic fibrosis can be diagnosed at birth, but most often is diagnosed during the early childhood years in young children (by the age of 3 years) who have had a history of respiratory infections, excessive fat in their stools, and who have poor weight gain. Nearly 8 percent of people with cystic fibrosis are diagnosed at 18 years of age or older because they have experienced only mild symptoms of cystic fibrosis. Because one of cystic fibrosis's major symptoms is respiratory infection, a cystic fibrosis diagnosis sometimes may be confused with other respiratory conditions such as asthma, pneumonia, or chronic bronchitis.

The methods and compositions of the present invention limit, reduce, lessen or eliminate one or more symptoms of cystic fibrosis. Symptoms of cystic fibrosis include but are not limited to: thick, viscous mucus secretions in the lungs; repeated infections: The accumulation of sticky, thick mucus in the lungs creates a favorable environment for infectious microorganisms to inhabit and flourish; stools, pale or clay colored, foul smelling, or stools that float; recurrent pneumonia; chronic cough, possibly with blood streaking; wheezing; bronchitis; chronic sinusitis; asthma; nasal polyps (fleshy growths inside the nose); weight loss, failure to thrive in infants, abdominal swelling; excessive salt in sweat, dehydration; failure of newborn to pass stool; abdominal pain, flatulence; fatigue; enlarged fingertips (clubbing); changes in color and amount of sputum (material coughed up from the lungs)

Conditions such as late onset of puberty, intestinal obstruction, inflammation of the pancreas, cirrhosis (a liver condition), and infertility may also be signs of cystic fibrosis. Cystic fibrosis symptoms does not follow the same pattern in all patients but affects different people in different ways and to varying degrees. However, the basic problem is the same—an abnormality in the glands, which produce or secrete sweat and mucus. Sweat cools the body; mucus lubricates the respiratory, digestive, and reproductive systems, and prevents tissues from drying out, protecting them from infection.

People with Cystic fibrosis lose excessive amounts of salt when they sweat. This can upset the balance of minerals in the blood, which may cause abnormal heart rhythms. Going into shock is also a risk.

Mucus in Cystic fibrosis patients is very thick and accumulates in the intestines and lungs. The result is malnutrition, poor growth, frequent respiratory infections, breathing difficulties, and eventually permanent lung damage. Lung disease is the usual cause of death in most patients. (Loss of lung function is a major medical problem in most patients with cystic fibrosis. The average person with cystic fibrosis experiences a gradual worsening of lung function each year due to infection and inflammation. In people with cystic fibrosis, loss of lung function primarily is caused by blockage of air passages with infected mucus. The thick mucus plugs the air passages of the lungs and must be broken up and removed. The repeated lung infections also can cause permanent scarring of the lungs. Many adults with cystic fibrosis also develop symptoms of chronic sinus infections.)

Cystic fibrosis can cause various other medical problems. These symptoms may include sinusitis (inflammation of the nasal sinuses, which are cavities in the skull behind, above, and on both sides of the nose), nasal polyps (fleshy growths inside the nose), clubbing (rounding and enlargement of fingers and toes), pneumothorax (rupture of lung tissue and trapping of air between the lung and the chest wall), hemoptysis (coughing of blood), cor pulmonale (enlargement of the right side of the heart), abdominal pain and discomfort, gassiness (too much gas in the intestine), and rectal prolapse (protrusion of the rectum through the anus). Liver disease, diabetes, inflammation of the pancreas and gallstones also occur in some people with Cystic fibrosis. (The pancreas secretes enzymes into the intestines to aid in the digestion of foods and liquids. However, patients with cystic fibrosis who suffer from pancreatic insufficiency do not secrete enough enzymes to derive proper nutritional benefit from their food. Also, the intestines are lined with thick, sticky mucus that prevents any secreted enzymes from reaching the food to be digested. Due to the inability to properly digest food, a person with cystic fibrosis produces large, greasy stools, which are lighter in color than normal and have a very foul odor. Patients also may suffer from abdominal cramping. To treat this problem, patients are given supplemental pancreatic enzymes that help them digest their food.

The pancreas also secretes insulin to process sugars. Some people with cystic fibrosis develop a specific type of diabetes called Cystic Fibrosis-Related Diabetes. Cystic fibrosis also can result in damage to the liver. In some patients with cystic fibrosis, the bile ducts, which transport bile from the liver to the intestines, become blocked. This condition can result in irreversible liver damage).

Huntington's disease is caused by a faulty gene and is diagnosed by detecting defective gene sequnce.
Most genes in the body are present in two copies, one from the mother and one from the father. The gene (which is called "Huntington") that causes Huntington's disease is dominant. This means that if a person inherits one copy of this gene from either parent, they will go on to develop the disease at some point in their life. A person who has one parent with Huntington's disease has a 50% chance of inheriting the faulty gene. This risk is 50% for each child and is not altered by gender or whether brothers and sisters are affected. Only people who have the faulty gene are capable of passing it on to their own children. Occasionally some people can develop the condition even though there is no family history of it. This is usually because previous generations were not diagnosed as a result of early death from other causes, or loss of contact through adoption.

Huntington's disease causes damage to brain cells in the areas of the brain involved in the control of movement, planning and motivation. People usually have symptoms for up to 10 years before they find out they have Huntington's disease. Most people are diagnosed between the ages of 30 and 50, although this can happen much earlier or later. Symptoms are often overlooked, as they are mild and commonly experienced by well people.

The methods and compositions of the present invention limit, reduce, lessen or eliminate one or more symptoms of Huntington's disease. Symptoms of Huntington's disease include but are not limited to: mild tremor, clumsiness, lack of concentration, difficulty remembering things, mood changes, including depression, sometimes, aggressive antisocial behavior.

As the disease continues, the symptoms become progressively worse, and lead to incapacitation. Physical symptoms include chorea (involuntary movements of the limbs, face and body). Chorea may lead to difficulty walking, speaking and swallowing. Choking is a particular hazard, due to reduced ability to control the muscles of the tongue, neck and diaphragm. People often lose weight because they have difficulty eating and burn more calories due to the continuous movement.

Emotional symptoms include depression, not only because of the burden of having a progressive disorder, but also as a direct result of the damage to certain brain cells. People often become frustrated at being unable to work or carry out previously simple tasks. They also seem to behave stubbornly, probably due to a reduced ability to react flexibly and to understand the needs and emotions of others. People with Huntington's may also become more irritable and antisocial than usual, or make inappropriate sexual advances.

Cognitive symptoms include a loss of drive and initiative. People with Huntington's may appear to be lazy or uninterested in life, spending days doing little or neglecting personal hygiene. They may also lose the ability to organise themselves, as planning skills and ability to carry out more than one task at once deteriorate. In later stages, people may get memory loss and be less able to understand speech. The behavioral changes that occur in people with Huntington's disease are often the most distressing for them, their family and their carriers. People with previously full and active lives gradually lose their independence and mobility. At the same time, their personality may become gradually more self-centered and apathetic, straining personal relationships.

A juvenile form of Huntington's disease also exists. Symptoms start before the age of 21 and the condition is usually inherited from the father. Symptoms are similar to those of adult Huntington's, but develop more rapidly and include muscular rigidity and fits.

The methods and compositions of the present invention limit, reduce, lessen or eliminate one or more symptoms of albinism. Albinism includes Hypopigmentation, oculocutaneous albinism and ocular albinism. Symptoms of nalbinism include but are not limited to: absence of pigment from the hair, skin, or iris of eyes; patchy absence of pigment (skin color, patchy); lighter than normal skin and hair, complete albinism; rapid eye movements (nystagmus); strabismus (eyes not tracking properly); photophobia (avoidance of light because of discomfort); decreased visual acuity and functional blindness. The disorders diagnosed by detection of physical symptoms or detection of the underlying genetic defects.

The oligonucleotide complex technique provided herein is a novel approach to modulation of genetic diseases, including but not limited to those diseases mentioned above. The oligonucleotide complex technique provides functional restoration of the mutated genes by deletion/insertion of a segment of RNA (or DNA). The oligonucleotide complex technique method inserts one or more deleted nucleotide(s) into the targeted region of specific RNA (or DNA). The oligonucleotide complex technique facilitates simultaneous correction of more then one mutation with a single set of oligonucleotide complex into a single targeted RNA (or DNA) gene.

Site-specific insertion of the specific RNA (or DNA) genes with the oligonucleotide complex technique may require one or more treatment steps with the oligonucleotide complex. Site-specific alteration of gene with the oligonucleotide complex technique may be performed in one or more targeted genes by using several oligonucleotide complex sets consecutively as required, or even simultaneously. For enhancing targeted gene repair efficiency using the oligonucleotide complex technique this complex is used synergistically with other known or potential therapeutic compounds. The oligonucleotide complex technique is used for targeting one or several harmful genes one by one or simultaneously. The oligonucleotide complex technique is used for extension of translation of targeted genes (by elimination of undesirable stop codons). The oligonucleotide complex technique is used for creation of "new genes" by insertion of transcription or translation sites in certain regions of the mammalian genome The oligonucleotide complex technique is used for deletion or insertion of purine or pyrimidine repeats at the ends of different genomic RNA or DNAs. The oligonucleotide complex technique is used for the deletion or diminution of a region of RNA containing a reiteration of excess triplets. The oligonucleotide complex technique provides insertion of UGU in a sufficient fraction of Δ508 mRNA to induce phenotypic reversion in a tissue culture cell line. The oligonucleotide complex technique according to SPQ data indicates suppression of the chloride anion conductance, or in the other words phenotypic restoration of a mutated Δ508 gene. The oligonucleotide complex technique according to subcloning data presented herein shows approximately 30 percent insertion of UGU in the site of the Δ508 mRNA UUU triplet deletion. The oligonucleotide complex technique is used for deletion or insertion of purine or pyrimidine repeats at the ends of specific genomic RNA or DNAs. The oligonucleotide complex technique inserts UGU in the site of the Δ508 mRNA UUU triplet deletion with one step addition of the oligonucleotide deletion/insertion hybridized RNA/modified RNA duplex. The oligonucleotide complex technique inserts UGU in the site of the Δ508 mRNA UUU triplet deletion with more than one (two) step treatment. The first step treatment was performed with RNase H (or other endonucleolytic enzyme) deleting single strand RNA. The second step of the treatment was performed by the oligonucleotide deletion/insertion RNA/modified RNA duplex. The oligonucleotide complex technique may require more then one step treatment (i.e. consecutive steps) for the restoration of targeted RNA (DNA) gene(s). RNase H (or other endonucleolytic enzyme) deletes a specific region of RNA, plus the pre-hybridized duplex of oligonucleotides involved in the oligonucleotide complex technique include, but are not limited to, standard oligonucleotides, modified oligonucleotides, standard and modified oligonucleotides with different sequential alteration, standard or modified oligonucleotide in the middle and flanked by different derivatives of oligonucleotides, derivatives of oligonucleotides facilitating different endonucleolytic deletions and/or some other "gene insertion/deletion" catalysis, oligonucleotides conjugated with different chemical groups (such as, but not limited to, intercalators, groove binders, alkylating reagents, photoactive groups (such as psoraren) and other moieties).

Compositions of oligonucleotide derivatives in the oligonucleotide complex technique include, but are not limited to standard and modified oligonucleotides with different sequential alteration. Oligonucleotide derivatives in the oligonucleotide complex technique may contain small chemical groups at the 5'- and/or 3'-end, including but not limited to, phosphate, diphosphate, triphosphate, thiophosphate, dithiophosphate, aldehyde, carboxyl, dihydroxyl, hydroxyl, methyl, ethyl, sulfhydryl, sulfate, Boronates, and similar chemical moieties. Oligonucleotide derivatives in the oligonucleotide complex technique may include, but are not limited to PNA; 2'-halo, 2'-fluoro, 2'-alkil, 2'-alkoxylalkyl, bridged sugars and similar chemical moieties; methylphosphonate, ethylphosphonate, phosphoramidate, thiophosphate, dithiophosphate, morpholino, Boronophosphate, morpholinophosphate internucleoside linkages and similar chemical moieties; oligonucleotides with derivatized heterocycles, sugars and/or internucleoside linkages and similar chemical moieties. Oligonucleotide derivatives in the oligonucleotide complex technique may include, but are not limited only to derivatized heterocycles, sugars or internucleoside linkages, but also to combination of these moieties mentioned above.

RNase H- (or other endonucleolytic enzyme-) activating single stranded oligonucleotide and pre-hybridized duplex of oligonucleotides involved in the oligonucleotide complex technique method may be four or more (up to three hundred) base long. The deletion/insertion oligonucleotide duplex used in the oligonucleotide complex technique method maybe composed of oligonucleotides of different length. The deletion/insertion oligonucleotide duplex employed in the oligonucleotide complex technique may possess the 5'- and/or 3'- "sticky ends". The length of "the sticky ends" in the deletion/insertion oligonucleotide duplex employed in the oligonucleotide complex technique may be one base and more (up to 40-60 bases). The double strand part of the deletion/insertion oligonucleotide duplex employed in the oligonucleotide complex technique may be 4-5 base pairs or more (up to 100 base pairs).

Sources of the derivatives of oligonucleotide used in the oligonucleotide complex technique method are chemically or biologically synthesized. The oligonucleotide complex technique is also useful to target with an oligonucleotide sequence specifically the deletion or insertion of a portion of a gene from a pathogenic bacterium, virus, insect, arthropod, parasite, land or marine plant or other living organism; to silence a virulence factor, thereby rendering that organism into a non-pathogenic one. This technique is used for preparation of a vaccine against the pathogen, or a therapeutic treatment by spray or other means of obtaining entry to the pathogen.

The oligonucleotide complex technique is used for the suppression/inactivation of biological pathogens in body fluids either in vitro, in vivo or ex vivo. The oligonucleotide complex technique is used for therapeutic purposes, diagnostic analytical purposes or as a tool for a laboratory research.

Cystic Fibrosis

Cystic Fibrosis (CF) is a lethal disorder caused by mutations in the CFTR gene encoding the CFTR channel [Riordan, et al., J. R., (1989) Science, 245, 1066-1073; Kerem et al., (1989) Science, 245, 1073-1080]; Burke (2003), Eng. J. Med. 349, 969-974]. CFTR, a cAMP-activated anion channel [Anderson et al., (1991) Science, 251, 679-682; Bear et al., (1992) Cell, 68, 809-818], is associated with the dysfunctionality of epithelia in several tissues [Crawford et al., (1991) Proc. Natl. Acad. Sci. USA 88, 9262-9266] including lungs, pancreas, intestine, sweat glands and kidneys. CF is the most common lethal genetic disease of Caucasians, affecting 1 in 2000 individuals. More than 150 mutations have been identified in the CFTR gene [Tsui, (1992) Trends Genet. 8, 391-398], associated with a pleiotropic spectrum of CF phenotypes [Cutting, (1993), J. Bioenerg. Biomembr. 25, 7-10; Strandvik et al., (2001), Genet. Test. 5, 235-242]. New mutations have been found with distinctive impacts on CF populations [Gilfillan et al., (1998), J. Med. Genet. 35, 122-125; Onay et al., (1998), Hum. Genet. 102, 224-230; Visich et al., (2002), Clin. Genet. 61, 207-213]. However, the most frequent CFTR mutation, accounting for almost 75% of all cases of the disease, is a deletion of three bases (TTT), encoding the amino acid phenylalanine in position 508 of the translation sequence, accompanied by C to U replacement immediately 5' to the deletion. This deletion is often accompanied by a mismatch immediately adjacent in the 5' direction to the deletion: in a U in place of a C.

The $\Delta$508 CFTR is a misfolded but partially functional channel protein [Li et al., (1993) Nature Genet. 3, 311-316; Pasyk et al., (1995) J. Biol. Chem. 270, 12347-12350], unable to translocate perfectly to target plasma membranes [Denning et al., (1992) Nature, 358, 761-764; Cheng at al., (1990), Cell, 63, 827-834]. Several chemical and pharmacological strategies have been attempted, to rescue the CF phenotype at the cellular level, to bring $\Delta$508 CFTR to the plasma membrane. Partial success has also been achieved by adenoviral vector infection [Boucher et al., (1994), Hum. Gene Ther. 5, 615-639; Teramoto et al., (1998), J. Virol. 72, 8904-8912] and re-insertion of the wild type CFTR gene into a CF genetic background. More recently, a novel repair strategy was used, based on trans-splicing of the $\Delta$508CFTR pre-mRNA [Liu at al., (2002), Biotechnol. 20, 47-52; Puttaraju et al., (2001), Mol. Ther. 4, 105-114; Mansfield et al., (2000) Gene Ther. 7, 1885-1895]. Gentamycin has also been found to induce a correction of faulty CFTR function in CF, caused by CFTR stop mutations [Bedwell et al., (1997) Nature Med., 3, 1280-1284], rather than by the TTT deletion.

Loss or suppression of disease-associated gene function by antisense oligonucleotide technologies involves specific inhibition of DNA, RNA and protein expression [Zamecnik et al., (1978), Proc. Natl. Acad. Sci. USA 74, 280-284; Stephenson et al., (1978) Proc. Natl. Acad. Sci. USA 75, 285-288]. This is based in good part on complementary hybridization of synthetic oligonucleotides with the natural sequences in either DNA or RNA [Temsamani et al., (1994) Antisense Res. Devel. 4, 279-284]. Triplex-forming oligonucleotides have also been used for the modification of cellular gene function [Felsenfeld et al., (1957) J. Am. Chem. Soc., 79, 2023-2024; Thoung et al., (1993) Angewandte Chemie. Intl. Ed. Eng., 32, 666-690; Agrawal et al., (1990). Proc. Natl. Acad. Sci. USA 87, 1401-1405]. The consequence of such interaction is a competitive blockade of either DNA or RNA synthesis at replication or transcription, respectively and, in the case of exons, at the translational steps in protein synthesis. Upon cell entry, exogenous complementary deoxyoligonucleotides hybridize with a target mRNA, inducing an excision endonucleolytic effect on the mRNA, a so-called ribonuclease H (RNAse H) effect resulting in synergism with hybridization inhibition [Zamecnik et al., (1996) Ed. By Sudhir Agrawal, Humana Press, NJ, 1-11]. Likewise, RNA editing [Simpson et al., (1996) Annu. Rev. Neurosci. 19, 27-52] has been reported in numerous cell systems where nucleotide sequences can also be modified at the RNA level. RNA editing encompasses various mechanisms, including base substitutions and deletions [Simpson et al., (1996) Annu. Rev. Neurosci. 19, 27-52]. RNA duplexes with internal and external guide sequences in some cases are required to drive these reactions.

Double stranded RNA sequences have a role in RNA interference (RNAi) and gene silencing at the transcriptional level [Hannon, (2002) Nature, 418, 244-251]. RNAi mediated gene silencing was discovered in *C. elegans* [Fire et al., (1998), Nature, 391, 806-811; Montgomery et al., (1998), Proc. Natl. Acad. Sci. USA 95, 15502-15507; Grishok et al., (2000), Science, 287, 2494-2497] and has been observed in numerous cell models and organisms [Hannon, (2002) Nature, 418, 244-251; Hammond et al., (2000), Nature, 404, 293-296; Silva at al., (2002), Trends Mol. Med. 8, 505-508]. Gene silencing results from successive cleavage of long dsRNA, particularly originating from viruses, to oligonucleotide siRNAs by DICER enzymes [Zamore et al., (2000) Cell, 101, 25-33; Bernstein et al., (2001), Nature, 409, 363-366]. After oligonucleotide hybridization of siRNA with mRNA, the cleavage of target mRNA is catalyzed [Hammond et al., (2000), Nature, 404, 293-296; Zamore et al., (2000) Cell, 101, 25-33]. RNAi phenomena have been used for target gene silencing from nematodes and plants to mammals [Hannon, (2002) Nature, 418, 244-251]. Separate from the above is CpG stimulation of host immunomodulatory mechanisms, in both prokaryotic and eukaryotic organisms [Krieg (2003) Nat. Med., 9, 831-835; Kandimalla et al., (2003) Biochemical Society Transactions, 31, 654-658].

The gain of function and/or correction of defective genes present a continuing challenge for gene therapy. Partial restoration of function in the Δ508 CFTR background has been shown to occur by membrane insertion of Δ508 CFTR without changes in either phenotype or genotype [Brown et al., (1996) Cell Stress & Chaperones, 1, 117-125; Arispe et al., (1998) J. Biol. Chem. 273, 5727-3574]. This is based on the capacity of Δ508 CFTR to function even as a misfolded protein [Welsh et al., (1993), Cell, 73, 1251-1254; Ward et al., (1994), J. Biol. Chem. 269, 25710-25718]. Its translocation to a plasma membrane may incompletely restore functionality of the phenotype RNA/DNA oligonucleotide hybrids [Cole-Strauss et al., (1996), Science, 273, 1386-1389; Yoon at al., (1996), Proc. Natl. Acad. Sci. USA 93, 2071-2076; Alexeev et al., (1998), Nature Biotech. 15, 1343-1346; Parekh-Olmedo et al., (2001), Sci. STKE 73, PL1] and single stranded oligonucleotides [Igoucheva et al., (2001) Gene Therapy, 8, 391-399] have been used for the correction of defective genes. Substituted, circular, single stranded RNA/DNA chimeras have been employed to insert base pairs in deficient genomic DNA [Cole-Strauss et al., (1996), Science, 273, 1386-1389; Yoon at al., (1996), Proc. Natl. Acad. Sci. USA 93, 2071-2076]. Nucleotide exchange of target episomic and genomic DNA is shown using chimeric RNA/DNA oligonucleotides. Some attempts at replicating this work, however, showed no nucleotide exchange in the targeted loci by cloning of the PCR products [Zhang et al., (1998) Antisense & Nucleic Acid Drug Developm. 8, 531-536]. Results were viewed by these and other investigators as PCR artifacts created by the RNA/DNA oligonucleotides themselves [Zhang et al., (1998) Antisense & Nucleic Acid Drug Developm. 8, 531-536; Taubes, (2002) Science, 298, 2116-2120]. Transcriptional repair has been used for repair of mRNA. Spliceosome mediated cis-splicing of pre-mRNA is an essential step in gene expression [Jurica et al., (2003), Mol. Cell, 12, 5-14]. Other trans-splicing mechanisms in pre-mRNA molecules have been shown to form functional hybrid mRNA molecules in different mammalian systems [Spector, (1993), Curr. Opin. Cell Biol. 5, 442-447; Harris et al., (1990), Nucleic Acids Res. 18, 3015-3019]. Spliceosome mediated RNA transplicing (SmaRT) technology has also been used to modify Δ508 CFTR transcripts in human CF airway epithelia [Liu at al., (2002), Biotechnol. 20, 47-52].

An mRNA hybridized to a single stranded synthetic short piece of DNA was used to activate RNase H [Agrawal et al., (1990). Proc. Natl. Acad. Sci. USA 87, 1401-1405], which then specifically hydrolyzed only the hybridized segment of mRNA. RNase H as an ubiquitous enzyme had been previously known [[Agrawal et al., (1990). Proc. Natl. Acad. Sci. USA 87, 1401-1405]]. The present invention defines nucleotide limits of RNase H activity in a precise way. At least a 4-6 nucleotide internally located region in an mRNA, which is hybridized to a phosphorothioate modified (PS) oligodeoxyribonucleotide, is needed for Rnase-mediated excision. If a precise small segment of mRNA, which included the deleted UUU region (the ribosomal substitute for TTT) were synthesized and annealed to the larger chimera, which induced/activated a small deletion in mRNA, an insertion of the somewhat larger total piece excised might restore the phenotypic effect at the mRNA level.

Initially, a modified oligodeoxyribonucleotide with a central segment containing a phosphorothioate (PS) modification was constructed, with flanking segments PS plus 2'-O-methyl modifications. This was designed to hybridize in Watson-Crick base complementarity to the region of Δ508 mRNA where the PS section would be directly opposite the Δ508 mRNA position, flanked 3'- and 5'- by an adjacent few nucleotides complementary to the Δ508 mRNA. In this way the PS segment would activate endogenous RNase H, and cleave those bases opposite the PS complementary oligonucleotide. The 2'-O-methyl PS, plus segments on both sides of the RNase H sensitive section would be generally nuclease and RNase H resistant and would serve in this way as a "genetic band aid". Without being limited by any particular mechanism, the flanking segments are intended to hold the 5'- and 3'-segments of Δ508 mRNA in place, in position for a possible insertion or repair of bases in a second step. For the possible repair step two single complementary strand oligonucleotides were constructed: Cystic Fibrosis 4 (CF4) and Cystic Fibrosis 6 (CF6), as shown in Scheme 1. This combination was annealed to form a duplex. The duplex was added to growing Δ508 CFTR cell cultures. Patch clamp examination [Reisin et al., (1994) J. Biol. Chem. 269, 20584-20591] showed evidence of phenotypic reversion (FIGS. 1 and 2). When the CF4/CF6 annealed duplex without oligonucleotide treatment, as described above, was, however, added to the tissue culture cells, phenotypic reversion was likewise found, based on the patch clamp technique. A one step phenotypic reversion technique was chosen, as a simpler model for the sequencing studies described below.

CF4 and CF6 were annealed to form an oligonucleotide duplex (CF4/CF6) (Table 1) and were then added to the Δ508 cells in tissue culture. There was restoration of the CFTR channel to functional normality, as determined by patch clamping and 6-methoxy-N-(3-sulfopropyl)quinolinium (SPQ) quenching techniques. Under those conditions, restoration of function was found to occur in 8-18 hours (FIGS. 1 and 2). As 2'-O-methyl modified CF4 has been reported not to activate RNase H [Shen et al., (1998) Bioorg. Med. Chem., 6, 1695-1705], there would appear to be another endonucleolytic enzyme responsible for the base excision, unless RNase H is activated by a triple-stranded oligonucleotide, in which the complementary 2'-O-methyl moiety is present.

Under Rose experimental conditions there was complete restoration of CFTR function, whereas non-insertion reversions have been only partial. [Rose D M et al, Eur J Res 2000; 5, 9-12] On replication of the human tissue culture cells and washing out of the oligonucleotide after a few days incubation, the restoration of CFTR function was lost. This strongly indicated a phenotypic but not genotypic (i.e. RNA but not DNA) restoration of functionality of the CFTR channel. Amplification and sequencing technology was used to determine whether trinucleotide insertion into Δ508 mRNA has been made. Scheme 1 is a schematic diagram of the insertional mechanism.

An oligonucleotide complex (CF4/CF6, respectively 2'-O-methyl RNA/unmodified RNA oligonucleotide duplex) was used herein to restore CFTR function by insertion of missing bases in Δ508CFTR mRNA from a cultured (Δ508) cell line. Cyclic AMP-activated (cAMP) whole cell currents and Cl-transport were detected in CF4/CF6 treated, rather than control Δ508 cells by the patch clamping and by SPQ fluorescence quenching analysis, respectively. Further, the nucleotide addition in the deleted region of Δ508 CFTR was determined after amplification by the Reverse Transcriptase-Polymerase Chain Reaction (RT-PCR). Insertion of UGU and replacement of U by C immediately 5' to the deletion site in Δ508 mRNA appear to have taken place, with phenotypic but not genotypic reversion in tissue culture of treated cells.

Genetic Diseases/Disorders

Suitable genetic diseases and sequences of appropriate targets in genes, such as those listed in U.S. Patent Application Publications 20030051270, 20030217377 and 20040014057, each incorporated herein by reference in there entireties, are treated using designed oligonucleotide complexes and the methods provided herein.

Several genetic diseases relate to disorders in the sequences of mutated genes and genes with inborn errors. Other major sources of genetic diseases, shown above, are due to "switch on" silent genes or presence of viral genes in the mammalian genome.

The cause of a fatal or serious genetic disease may be as small as a single mismatch in base pair (one mismatch, one inserted/deleted base pair in the whole gene sequence) or absence of a partial or whole gene in the genome. Consequently, availability of the highly specific oligonucleotide complex technique for the restoration of the targeted (defected) gene could be a powerful tool to combat currently incurable genetic diseases.

Oligonucleotide complexes and methods for their use for the functional restoration of the mutated genes by deletion/insertion mechanism of the segment of RNA are provided. Site-specific insertion of the genes with the oligonucleotide complex technique (as shown herein as replacement of a cystic fibrosis phenotype in a cultured Δ508CFTR cell line experiments) can occur with a one or two step oligonucleotide complex treatment. Below are shown schemes for restoration of mutated and inborn error genes (Schemes 2-7), and schemes of switch-on and/or switch-off targeted genes (Schemes 8-10) using an oligonucleotide complex technique.

One step and two step oligonucleotide complex treatment of targeted RNA (or DNA) are shown in the Schemes 3, 5, 7, 9 and 2, 4, 6, 8, 10 respectively.

Scheme 2 shows a site-specific deletion/insertion mechanism at the targeted region of RNA with the two-step oligonucleotide complex technique. The targeted region in this scheme could be one (or a few) mismatched bases or one (or a few) inserted bases in the RNA sequence. On the first step, oligonucleotide for RNase-H activation deletes the target region of RNA, and on the second step insertion of the desirable sequence takes place. The RNase H deleted region could be a few or more bases, depending on the extend of RNase induced deletion, as a result of which the RNA oligonucleotide from the insertion duplex might be spliced into the deleted region, or alternatively serve as a triplex backbone sequence for a one-by-one insertion mechanism.

Scheme 3 shows a site-specific deletion/insertion mechanism of the targeted region of RNA with the one step oligonucleotide complex technique. There are different possibilities of one step restoration: triplex backbone sequence formation by a one-by-one insertion mechanism, with specific docking and cleavage of selective nucleotide sequences, which are hybridized to an RNA (or DNA) sequence. The cleavage might by induced by either a new enzyme or the Dicer enzyme, and as a result, production of RNA (or DNA) with a corrected (inserted) region.

Scheme 4 shows site-specific insertion mechanism of the deleted region of RNA with the two-step oligonucleotide complex technique. Schemes 6, 8 and 10 show a site-specific insertion/deletion mechanism at the targeted regions of RNA (or DNA) with the two-step oligonucleotide complex technique. RNA (such as Huntington's disease) in Scheme 6 contains reiteration of excess triplets, and accordingly the purpose of the deletion step is to cut out the excess repeats. RNA shown in Scheme 8 is a model of active (harmful) RNAs and the goal of the insertion is to switch off these RNAs. The purpose of the insertion shown in Scheme 10 (opposite of Scheme 8) is to "wake up" a silent gene or to create new one. The insertion shown in Schemes 2, 4, 6, 8 and 10 could proceed with similar mechanisms, but goals achieved for each of the approach would be different.

The purpose of the approaches shown in Schemes 5, 7 and 9 is identical to the Schemes 4, 6 and 8. The deletion/insertion mechanism of the targeted region of RNA, shown on Schemes 5, 7 and 9, proceeds with the one step oligonucleotide complex technique, as described for Scheme 3.

Schemes 11 and 12 show schemes for repair of an inactive tyrosinase gene by one and two step oligonucleotide complex approaches, respectively. The schemes contain one of the possible versions of the oligonucleotide complex which may be used for the replacement of mutated C with G in inactive tyrosinase mRNA. This type of alteration can achieve a phenotypic restoration of the mutated tyrosinase gene.

Schemes 13 and 14 show schemes for repair of Cystic Fibrosis Δ508 mRNA by one and two step oligonucleotide complex treatment approach. As described herein, mutated Δ508 mRNA contains two defects: first, absence of a UUU triplet at Δ508 region and change of U to a C immediately 5' to the same Δ508 position. Because of the close location of both mutations one set of oligonucleotide complex was sufficient for repair of both defects.

In some cases the targeted gene might contain more then one mismatch or inserted (deleted) region, which may be distantly located. For restoration of such genes it would be appropriate to use two or more oligonucleotide complex sets consecutively or simultaneously.

For enhancing targeted gene repair efficiency of oligonucleotide complex, the complex could be used synergistically with other known or potential therapeutic compounds.

This application claims priority to U.S. Ser. No. 60/557,732, filed on Mar. 29, 2004 and U.S. Ser. No. 60/560,026, filed on Apr. 7, 2004, each of which is incorporated herein by reference in their entireties. Further, the contents of all references cited are incorporated in their entireties herein by reference. Practice of the invention will be more fully understood from the following examples, which are presented herein for illustration only and should not be considered as limiting the invention in any way.

EXAMPLES

The examples provided herein demonstrate feasibility of using an oligonucleotide complex technique as a therapeutic and/or prophylactic agent for the phenotypic and restoration of function of a mutated gene. The following Material and Methods were used throughout the Examples.

Oligonucleotide Synthesis

DNA and RNA oligonucleotides (Table 1) were synthesized on a 394 DNA/RNA synthesizer (Applied Biosystems) with phosphoramidite chemistry and standard phosphoramidite monomers from Glen Research. For the introduction of 3' and 5' phosphate groups on the CF4 oligonucleotide (Table 1), 5'- and 3'-phosphorylation reagents were used accordingly (Glen Research). Phosphorothioate bonds were introduced by sulfurization with Beaucage thiolating reagent [Padmapriya et al., (1994) Antisense Res. Dev. 4, 185-199]. 2'-O-methyl modifications, oligoribonucleotides and phosphorothioate oligonucleotides were synthesized, and HPLC purified as described [Metelev et al., (1994) Bioorg. Med. Chem. Lett. 4, 2929-2934; Agrawal et al., (1998) Antisense Nucleic Acid Drug Dev. 8, 135-139].

Annealing of CF4/CF6 Oligonucleotide Duplex

Stock solutions of CF4 (1 mM) and CF6 (1 mM) were prepared by dissolving compounds in high ionic strength buffer (0.2 M NaCl, 20 mM $MgCl_2$, 20 mM Tris-HCl, pH 7.0). Duplex formation was prepared with 1:1 (v:v) mixture of compounds, by heating to 75-80° C., and cooling down gradually to room temperature. All duplexes and compounds were sterilized by passage through 0.45 µm cellulose acetate centrifuge filters (Costar).

Cell Culture and Incubation

Mouse mammary carcinoma cells (c127i) transfected with human epithelial CFTR wild type (WT1) or Δ508 CFTR cells [Cantiello et al., (1994), J. Biol. Chem. 269, 11224-11232; Dechecchi et al., (1993) J. Biol. Chem. 268, 11321-11325] were used for these studies. The transfected c127i cells are high level producers of Δ508 CFTR mRNA. Cells were grown and maintained in Dulbecco's medium (DMEM), supplemented with 10% fetal bovine serum and 1% L-glutamine, as previously reported [Verkman, (1990) Am. J. Physiol. 259, C375-C388].

Electrophysiology

Whole-cell and excised inside-out patches were obtained to assess cAMP-PKA dependent anion currents in treated Δ508 cells. Currents and command voltages were obtained and driven. respectively, with a Dagan 3900 amplifier using a 1 gigaohm headstage. The excised patch-clamp configuration was carried out as previously described [Reisin et al., (1994) J. Biol. Chem. 269, 20584-20591]. Single channel data were obtained between ±100 mV in symmetrical $Cl^-$. Data were further analyzed as previously described [Reisin et al., (1994) J. Biol. Chem. 269, 20584-20591]. The pipette and bathing solution contained, in mmol/L, either: NaCl 140, $MgCl_2$ 1.0, KCl 5, and N-2-hydroxyethylpiperazine N'-2-ethanesulfonic acid (HEPES) 10, at pH 7.4, or $MgCl_2$ 70, HEPES 10, pH 7.4. The bathing solution also contained 1.0 mmol/L $CaCl_2$. Whenever indicated, the patch-pipette was filled up to at least one third of its height with either MgATP or TrisATP (100 mmol/L, pH 7.4 adjusted with N-methyl-glucamine) as previously reported [Reisin et al., (1994) J. Biol. Chem. 269, 20584-20591]. Experiments were conducted at room temperature. The cAMP stimulatory mixture contained 8-Br-cAMP, isobutyl-methyl-xanthine (IBMX) and forskolin. Final concentrations were 500 µmol/L, 200 mol/L, and 10 µmol/L, respectively. The catalytic subunit of PKA was used at a final concentration of 20 µg/ml. The $Cl^-$ channel blocker, diphenylamine-2-carboxylate (DPC) was kept in a 100-fold stock solution (20 mmol/L) in 50% water/ethanol. DPC was used at a final concentration of 500 µM.

SPQ Fluorescence

Cyclic-AMP-stimulated CF transport was also followed by fluorescence changes of cells loaded with the $Cl^-$ sensitive dye 6-methoxy-N-(3-sulfopropyl)quinolinium (SPQ) [Verkman, (1990) Am. J. Physiol. 259, C375-C388]. Briefly, cells were grown to partial confluence on glass coverslips. SPQ cell loading was conducted by a15-min incubation in a $Cl^-$ free diluted salt solution containing SPQ (5 mM). The saline solution contained 135 mM Natgluconate, 2.0 mM $KH_2PO_4$, 1.0 mM $MgSO_4$, 1.0 mM $Ca^{2+}$-gluconate, and 10 mM HEPES (pH 7.4). In some experiments, gluconate was replaced by either isethionate or aspartate with similar results. SPQ fluorescence was determined under an oil immersion X20 objective in a Nikon E-800 fluorescence microscope (Tokyo, Japan), with an UV filter (96101C UV-2E/C). Images were captured with a Hamamatsu (C4742-95) digital camera and stored as TIFF files in a Macintosh computer with the IPLab Spectrum software (Signal Analysis Corp.). Pictures were analyzed digitally with the NIH Image 1.62b7 software. SPQ cytoplasmic fluorescence values were normalized between intra-nuclear (considered as zero quenching, i.e. low $Cl^-$), and extracellular background. Data were expressed as percent fluorescence with respect to time zero, the time when cells were placed in an isotonic saline solution. The solution contained 135 mM NaCl, 2.0 mM $KH_2PO_4$, 1.0 mM $MgSO_4$, 1.0 mM $Ca^{2+}$-gluconate, 10 mM HEPES (pH 7.4), with or without the cAMP stimulatory combination mixture.

Primers and RT-PCR of Δ508CFTR mRNA

Total RNA isolated by Trizol® reagent according to the manufacturer's protocol (Invitrogen, CA) from either WT1 or Δ508 cells treated with or without CF6/CF4 annealed duplex oligonucleotides (final concentration of duplex in reaction mixture 10 µM) was used to perform the RT-PCR assay [Kleppe et al., (1971) J. Mol. Biol. 56, 341-361] in two steps by using a ThermoScript RT-PCR system (GIBCO, BRL). Several sets of primers were used (see CF Table 1). In the first step, total RNA (~2 µg) was incubated for 60 min at 55° C. with amplification refractory mutation system (ARMS) [Ferric et al., (1992) Am. J. Hum. Genet. 51, 251-262] reverse mutant (M1) and normal (N1) primers (0.5 µg each) separately for the first-strand synthesis. In a second step, after heating at 94° C. for 5 min, 35 cycles of PCR were carried out on the samples. PCR cycles were performed first by denaturation at 94° C. for 2 min, annealing at 62° C. for 1 min, and extension at 72° C. for 2 min, followed by a final extension for 10 min at 72° C. Two ARMS reverse primers (N1 and M1) [Ferric et al., (1992) Am. J. Hum. Genet. 51, 251-262], and a forward (F1) primer were used (Table 1). Similarly RT-PCR was performed with ARMS PS reverse primer (SCFR) and PS forward primer (SNF1, Table 1). RT-PCR products were separated in 3% agarose gel and subjected to automated DNA sequence analysis.

Similarly, RT-PCR was conducted using allele specific primers (Scheme 1B, Table 1) as follows. In the first step, total RNA (~2 µg) was incubated for 60 min at 55° C. with reverse (CFR) primer (0.5 µg each) for the first-strand synthesis. In a second step, samples were heated at 94° C. for 1 min. PCR was performed for thirty cycles at 60° C. including denaturation at 94° C. (45 sec), annealing at 60°

C. (45 sec), and extension at 72° C. for 1 min. This procedure was ended with a seven-minute final extension at 72° C. Two forward primers (CFW and CFM) and one reverse primer (CFR) were used for allele specific RT-PCR (Table 1). The RT-PCR assay was performed with the MasterAmp™ RT-PCR system (Epicentre, WI). In this procedure, combined reverse transcription and PCR were performed in the presence of forward normal (NF1) and mutant (MF2) and reverse (CFR) primers (0.5 µg each) separately. First, samples were incubated for 20 min at 60° C. PCR was performed for 40 cycles at 94° C., denaturation for 30 sec, annealing at 62° C. for 30 sec and 72° C. extension for 1 min. The reaction ended by a final extension for 6 min at 72° C. Two forward primers (NF1 and MF2) and a reverse primer (CFR) were used for this procedure. RT-PCR products were separated in a 3% agarose gel and were then subjected to automated DNA sequence analysis. ThermoScript RT-PCR products obtained by ARMS primers were subcloned for further separation and purification of possible heterogeneity of oligomers so obtained in pCR-Blunt vector, according to the manufacturer's protocol (Invitrogen, CA). The resulting clones were subjected to automated DNA sequence analysis using a T7 promoter primer.

Example 1

Restoration of Δ508CFTR Phenotype

To restore the normal (wild type) phenotype in cells expressing Δ508CFTR, modified oligonucleotides were constructed and their effect on ion transport was assessed in Δ508 cells treated with these constructs. In a first step, a modified oligodeoxyribonucleotide was synthesized, containing phosphorothioate (PS) and PS plus 2'-O-methyl modifications for the central and flanking segments, respectively. This oligonucleotide was designed to hybridize in Watson-Crick base complementarity to the region of Δ508 mRNA where the PS section would be directly opposite the Δ508 mRNA position, flanked 3'- and 5'- by adjacent nucleotides complementary to the Δ508 mRNA. Accordingly, the PS segment would activate endogenous RNase H, and cleave those bases opposite the PS complementary oligonucleotide (10 µM). The insertion of bases then occurs in a second step.

For the second or insertion step, two complementary single strand oligonucleotides, CF4 and CF6 (Table 1, Scheme 1A) were constructed. The annealed CF4/CF6 duplex (10 µM final concentration) was added to the Δ508 CFTR cells after 2 hours incubation, then washout, in the deletion step. Next, following overnight or up to 72 hour incubation in the second (insertion) step, patch clamp examination was conducted on the treated cells.

Whole cell currents of two step treated Δ508 cells (FIG. 1) showed a 243% increase after cAMP stimulation (2.98±0.68 nS/Cell vs. 0.87±0.16 nS/Cell, n=24, p<0.01), which was absent in the control Δ508 cells (FIG. 1). The cAMP-activated currents were largely (>84%) inhibited by the CFTR inhibitor DPC (500 µM) as expected for wild type CFTR. Similar results were obtained with WT1 cells, overexpressing wild type CFTR in the same cellular background. The treated Δ508 cells (10/12) displayed PKA and ATP activated 10-12 pS Cl$^-$ channels (FIG. 2) not observed in the control Δ508 cells (0/24).

When the CF4/CF6 annealed duplex was, however, added to the tissue culture cells without performing a first oligonucleotide treatment step as described above, phenotypic reversion was likewise found, as determined by the patch clamp technique. Thus, a one step phenotypic reversion technique was chosen as a simpler model for the sequencing studies described below.

Surprisingly, CF4/CF6 cells sporadically showed large, DPC inhibitable whole-cell currents in the absence of cAMP simulation (data not shown). Both WT1 and CF4/CF6 treated Δ508 cells responded with a comparably similar change in SPQ fluorescence in response to cAMP stimulation (FIG. 3) [Ram et al., (1989) Proc. Natl. Acad. Sci. USA 86, 10166-10170]. Control Δ508 cells showed no cAMP-induced change in SPQ fluorescence (FIG. 3). The data indicate that CF4/CF6 treatment of Δ508 cells restores a normal tissue culture phenotype, consistent with the presence of functional CFTR.

Example 2

Sequencing Analysis of PCR Products

In order to determine the extent of restored phenotype in the CF4/CF6 treated Δ508 cells, total RNA was isolated and CFTR specific primers were used to amplify the predicted region. CFTR wild type specific primers efficiently amplified single bands of the expected size in the CF4/CF6 oligonucleotide treated cells. The sequence region after this treatment did not show changes in the PCR amplified oligonucleotides when wild type primers were used. Because the number of Δ508 mRNA copies that are potentially repaired may be low, allele specific primers for either wild type or mutated CFTR were used next (CFFW and CFFM, Table 1).

Allele specific primers detected mRNA from serial dilutions of wild and Δ508 total RNA by means of a shift of the amplified band (FIG. 4). Wild type RT-PCR product could be detected in 1:10,000 dilutions in Δ508 mRNA background (FIG. 4). Initially, RT-PCR product from the allele specific wild type primer (CFFW, Table 1) in the oligonucleotide treated Δ508 cells also failed to detect insertion in the amplified band. Therefore, total RNA of CF4/CF6 treated Δ508 cells were further tested by PCR analysis with ARMS specific primers (FIG. 5) [Skerra, (1992) Nucleic Acid Res. 20, 3551-3554]. Wild type and mutated ARMS primer-amplified PCR bands were examined by DNA sequence analysis. The sequence of the amplified mutated cDNA showed a variety of one-codon insertions, rich in G residues. Whether a GGG codon (glycine) is an acceptable substitute for phenylalanine remains to be determined, since systematic study of such base insertion has not been done to our knowledge.

To analyze this observation further, the PCR products were subcloned in pCR-Blunt vector and subjected to DNA sequence analysis. The fraction of control RNAs isolated from untreated Δ508 cells showed no oligonucleotide insertion. However, mRNA isolated from CF4/CF6 treated Δ508 cells showed 20-30% UGU insertion, based on analysis of the percentage of subclones showing TGT insertion into the RT-PCR generated Δ508 DNA. This percentage of insertion is apparently sufficient for phenotypic reversion in the tissue culture system. None of the subcloned untreated Δ508 cells displayed false positives (three-base insertion) in the region flanking the initial deletion (FIG. 6). Combined reverse transcription and PCR were performed with forward wild type (NF1) and mutant (MF2), and reverse (CFR) primers (0.5 µg each) separately. Insertion of bases in the proper position (Scheme 1B) has been found in subcloned and sequenced RT-PCR products, from treated but not control Δ508 cells.

Without being limited by any particular mechanism, the hypothesis was tested as to whether base insertion in the treated Δ508 cells has occurred at the RNA level. It was possible that the repair mechanism was carried out instead of/or in addition to, the DNA level, by way of reverse transcription extending back to the genome. This was tested by RT-PCR analysis of DNA from subcloned Δ508 cells originally treated with CF4/CF6. No evidence was obtained that the restored phenotype was carried back to the inheritable DNA genome level was obtained. Western blot analysis was conducted with antibodies targeted to epitopes upstream and downstream of the Δ508 deletion, respectively. The data indicate that the full-length protein was made in the presence of the oligonucleotides.

Further, the data rule out that partially degraded protein was being translated after treatment with the oligonucleotides because of stop codon missing signals in the treated mRNA [Bedwell et al., (1997) Nature Med., 3, 1280-1284]. Both antibodies showed the same level of protein, without shorter, truncated or degraded peptides. Thus, treatment with CF4/CF6 does not act as an inhibitor of protein synthesis.

Example 3

Mechanism of Insertion

As an initial step, restoration was sought of the most common CF phenotype by antisense oligodeoxynucleotide hybridization to the region immediately adjacent to the trinucleotide deletion, on both sides of the Δ508CFTR mRNA. The double-stranded synthetic 2'-O-methyl-RNA/ unmodified-RNA oligonucleotide chimera (CF4/CF6) was constructed and used to anneal, selectively cut, and repair the missing region (Scheme 1B). This duplex, as shown, contains a single stranded 2'-O-methyl-substituted 33-mer oligoribonucleotide (CF4) hybridized to an unmodified 11-mer oligoribonucleotide with 5' and 3' monophosphate termini (CF6). The role of the 5'- and 3'-phosphate termini of CF6, if any, remains to be determined. The CF4/CF6 chimera may theoretically hybridize with the mRNA bearing the deletion (Scheme 1B), followed by an mRNA cleavage step, as a result of which CF6 might theoretically be spliced into this region or alternatively, serve as a triplex backbone sequence for a one-by-one insertion mechanism.

Without being limited by any particular mechanism, the mismatch created by using the oligonucleotides provided herein and found immediately proximal in the 5'-direction to the Δ508 mRNA UUU deletion may induce an as yet unknown deletion mechanism. For one, the deletion step may be induced by either a new enzyme or by the Dicer enzyme. Another possibility is that RNAse H, in the presence of a triplex, may induce the deletion. There may conceivably be a deletion in RNA analogous to the MutS DNA mismatch mechanism [Wang et al., (2003) Proc. Natl. Acad. Sci. USA 100, 14822-14827]. The process by which CF4/CF6 restores the phenotype is consistent with specific docking and cleavage of selective nucleotide sequences hybridized to an mRNA sequence. A -TTT- insertion into the PCR amplified deoxyoligonucleotide would be expected, if the -UUU- from CF6 had been inserted into the Δ508 mRNA. However, TGT (UGU in the Δ508 mRNA) insertion was consistently observed in clones obtained by ARMS primers amplification RT-PCR products (Scheme 1B and FIG. 6). This finding suggests a one-by-one insertion mechanism, with a G in place of a U.

Initial sequencing of RT-PCR oligodeoxynucleotides obtained with ARMS primers specific for the CFTR wild type sequence (N1, Table 1) revealed the presence of a mixture of residues rich in G's in the Δ508 site. Subcloning of this oligodeoxynucleotide band resulted in the finding that some but not all of the sequenced cDNA material expressed a TGT at this Δ508 site. Since it was mRNA that was subjected to RT-PCR amplification, the corresponding bases in the Δ508 region were actually UGU. The G residue in the UGU could be accounted for by a restoration mechanism with other than Watson-Crick complementarity in insertion [Yang et al., (2003) Proc. Natl. Acad. Sci. USA 100, 15376-15380]. The 3' hybridization initial steps enabled by the ARMS primers may also be flawed by exonucleotide-induced primer degradation in the reverse transcriptase step of the RT-PCR amplification procedure [Skerra, (1992) Nucleic Acid Res. 20, 3551-3554; Smith at al., (2003) Proc. Natl. Acad. Sci. USA 100, 15440-15445]. Other possibilities of error introduction [Kobayashi et al., (1990) Am. J. Hum. Genet. 47, 611-615], may explain the apparently artifactual deletions shown in Scheme 1B which accompany insertions. This consideration was partially confirmed by wild type ARMS primer-RT-PCR product amplification of the sequence in WT1 cells, which only carries wild type CFTR. In this reaction, the expected -TTT- was found by sequence analysis of the wild type RT-PCR material, in contrast to the TGT (actually UGU in mRNA) when the repaired Δ508 mRNA was sequenced.

For further clarification of the above results, new sets of primers were constructed with an initial phosphorothioate substituted nucleotide in the 3' end, followed by several (PO) standard nucleotides. This improved primer selectively amplified CF4/CF6 treated, but not control (untreated) RT-PCR product in Δ508 cells. The ARMS forward PS primer (SNF1) inserts UGU without a concomitant new deletion (Scheme 1B, Table 1), thus presenting the best case for phenotypic reversion to wild type. Just 5' to the UUU in the wild type CFTR is a C residue, while in the mutant Δ508 CFTR this residue is a U. This may conceivably result in replacement failure 5' to the inserted UGU using the ARMS reverse primer (N1). The purpose in using CF4/CF6 complex, which has a G residue rather than U proximal to the 5' end of the Δ508 deletion, was to make this residue complementary to that in the wild type sequence rather than in the deleted Δ508 sequence. Both AUC and AUU code for isoleucine. This base mismatch for the Δ508 mRNA (CF Scheme 1) may however induce a single strand break, analogous to that found for single DNA mismatches as mentioned above [Wang et al., (2003) Proc. Natl. Acad. Sci. USA 100, 14822-14827], necessary for a subsequent repair mechanism to be initiated. This eliminates the possibility that the change of C to a U, immediately 5' to the TTT in the same position in the Δ508 gene may contribute, in addition to the Δ508 TTT deletion, to the phenotypic change in CFTR.

DNA polymerase has a high degree of Watson-Crick fidelity in synthesizing complementary strands. Reverse transcriptase, which starts at the 3'-end of the PCR amplification, however, has a lower level of this specific type of fidelity. This property of reverse transcriptase may be a possible explanation for the UGU (the equivalent of TGT) found in the amplified, restored Δ508 mRNA. In relation to phenotypic restoration, benign mutations of the TTT present in the wild type gene do exist. TGT is one of these, coding for cysteine, which appears to be an acceptable substitute for phenylalanine in the Δ508 region [Kobayashi et al., (1990) Am. J. Hum. Genet. 47, 611-615]. The 2'-O-methyl group, plus the 5-methyl of thymidine, which uridine does not have, may also alter the tertiary structure of the CF4 chimera. Such factors may influence the nucleophilicity, electrophilicity, and polarizability of the bases, which make up the mRNA-CF4/CF6 triple-stranded structure. Tinoco and colleagues have described numerous double stranded DNA/RNA base complementarities which conformational and other experimental molecular conditions may cause to favor over the standard Watson-Crick AT and GC ones [Burkard at al., (1999) In The RNA World. editors. Cold Spring Harbor Lab. Press, New York. 675-680]. The highly sensitive nanosphere/gold procedure of Letsinger and colleagues [Taton et al., (2000) Science, 289, 1757-1759; Letsinger at al., (2000) Bioconj. Chem. 1, 289-291] may in the future be applicable as an alternative to the PCR technique, avoiding possible artifacts introduced by PCR amplification, or else may be used following subcloning.

The data herein indicate that specific base insertion in ∆508 mRNA has been made. Certain PCR-introduced artifacts have been avoided by phosphorothioate modification of the 3'-terminal residues of ARMS specific primers. Under our best conditions thus far, insertion of UGU has taken place in a sufficient fraction of ∆508 mRNA to induce phenotypic but not genotypic reversion in a tissue culture cell line. The subcloning data showed 20-30 percent insertion of UGU in the site of the ∆508 mRNA UUU triplet deletion.

Example 4

Regulation of Huntingtin Protein Gene and Oculocutaneous Albinism Aim-1 Gene

The methods of the instant invention have also been applied to the genetic disorders Huntington's disease and Albinism. Specifically, the gene deletion/insertion mechanism has been applied to the Huntingtin protein gene [Cell 72: 971-983, 1993] and the Oculocutaneous Albinism Aim-1 gene [J Biol Chem. 2002 Jan. 4; 277(1):402-6].

The gene deletion/insertion for the Huntingtin gene inhibits translation of Huntingtin protein, which synthesizes too many consecutive glutamine residues. Oligonucleotide compounds have been prepared for this inhibitory purpose (Table 2). Deletion of two codons of mRNA (+10+15 from translation site) and insertion stop codons (UAA) can inhibit translation of Huntingtin protein. Table 2 shows the HT3 and HT4/HT6 oligonucleotides and Scheme 15 shows the insertion into the gene for Huntingtin protein with HT3 followed by HT4/HT6 duplex oligonucleotides. Scheme 15 can presumably be carried out in a one step process using the HT4/HT6 oligonucleotide complex.

Absence of 7 bases in Aim-1 gene is the cause of Oculocutaneous albinism. The gene deletion/insertion mechanism can be utilized for the Aim-1 gene as shown in Scheme 16. Oligonucleotide compounds have been prepared for this purpose (Table 2). Table 2 shows the Alb3 and Alb4/Alb6 oligonucleotides and Scheme 16 shows the insertion into the Aim-1 gene with Alb3 followed by Alb4/Alb6 duplex oligonucleotides. Scheme 16 can presumably be carried out in a one step process using the Alb4/Alb6 oligonucleotide complex.

TABLE 1

Sequences of oligonucleotides used (5' > 3')

| | | |
|---|---|---|
| CF4 | auc aua gga aac acc aaa gau gau auu uuc uuu | (SEQ ID NO: 1) |
| CF6 | pC AUC UUU GGU Gp | (SEQ ID NO: 2) |
| F1 | GGG AGA ACT GGA GCC TTC A | (SEQ ID NO: 3) |
| N1 | GTA TCT ATA TTC ATC ATA GGA AAC ACC ACA | (SEQ ID NO: 4) |
| M1 | GTA TCT ATA TTC ATC ATA GGA AAC ACC ATT | (SEQ ID NO: 5) |
| NF1 | GCC TGG CAC CAT TAA AGA AAA TAT CAT CTT | (SEQ ID NO: 6) |
| MF2 | GCC TGG CAC CAT TAA AGA AAA TAT CAT TGG | (SEQ ID NO: 7) |
| CFR | GTT GGC ATG CTT TGA TGA CGC TTC | (SEQ ID NO: 8) |
| CFFW | GGC ACC ATT AAA GAA AAT ATC ATC TT | (SEQ ID NO: 9) |
| CFFM | GGC ACC ATT AAA GAA AAT ATC ATT GG | (SEQ ID NO: 10) |
| SCFR | GTT GGC ATG CTT TGA TGA CGC TTC | (SEQ ID NO: 11) |
| SNF1 | GCC TGG CAC CAT TAA AGA AAA TAT CAT CTT | (SEQ ID NO: 12) |
| SMF2 | GCC TGG CAC CAT TAA AGA AAA TAT CAT TGG | (SEQ ID NO: 13) |

Primers and constructs used to repair CFTR mRNA. Lower case letter are a nucleotide sequence in CF4 corresponding to bases of 2'-O-methylribosyl oligonucleotides, with internucleoside phosphate bonds. Upper case letter are a nucleotide sequence in CF6 corresponds to natural RNA sequences and small case p corresponds to the terminal phosphate groups. Bold type corresponds to the natural DNA sequences. Shaded region in SCFR, SNF1 and SMF2 corresponds to internucleoside phosphorothioate bonds.

TABLE 2

Sequences of oligonucleotides used (5' > 3')

| | | |
|---|---|---|
| HT3 | CAG CTT TTC CTG GGT CGC | (SEQ ID NO: 14) |
| HT4 | GGC CTT CAT CAG xTT TTA GGT CGC CAT GGC GGT | (SEQ ID NO: 15) |
| HT6 | pAC CUA AAAp | (SEQ ID NO: 16) |
| Alb3 | GCU GAC AGC CCU | (SEQ ID NO: 17) |
| Alb6 | pGCU CGU CGC U GUCp | (SEQ ID NO: 18) |
| Alb4 | CCA CUG GCU GAC A GCG ACG AGC CCU GAG GGU | (SEQ ID NO : 19) |

Primers and constructs used to repair Huntingtin protein gene and the Oculocutaneous Albinism Aim-1 gene

OTHER EMBODIMENTS

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. Other aspects, advantages, and modifications are considered to be within the scope of the following claims. The claims presented are representative of the inventions disclosed herein. Other, unclaimed inventions are also contemplated. Applicants reserve the right to pursue such inventions in later claims.

What is claimed is:

1. An oligonucleotide about 33 nucleotides in length comprising the sequence AUCAUAGGAAACAC-CAAAGAUGAUAUUUUCUUU (SEQ ID NO:1), wherein the oligonucleotide comprises an RNase H-resistant modification.

2. The oligonucleotide of claim 1, wherein said oligonucleotide is 33 nucleotides in length.

3. The oligonucleotide of claim 2, wherein said modification is a 2'-O-methyl ribosyl modification.

4. The oligonucleotide of claim 3, wherein each nucleotide in said oligonucleotide is a 2'-O-methylribosyl nucleotide.

5. A composition comprising the oligonucleotide of claim 1.

6. The oligonucleotide of claim 1, wherein said modification is a 2'-O-methyl ribosyl modification.

7. The oligonucleotide of claim 6, wherein each nucleotide in said oligonucleotide is a 2'-O-methylribosyl nucleotide.

8. A composition comprising the oligonucleotide of claim 2.

9. A composition comprising the oligonucleotide of claim 3.

10. A composition comprising the oligonucleotide of claim 4.

* * * * *

SEQUENCE LISTING

```
<160> NUMBER OF SEQ ID NOS: 60

<210> SEQ ID NO 1
<211> LENGTH: 33
<212> TYPE: RNA
<213> ORGANISM: Homo sapiens

<400> SEQUENCE: 1
aucauaggaa acaccaaaga ugauauuuuc uuu                                    33

<210> SEQ ID NO 2
<211> LENGTH: 11
<212> TYPE: RNA
<213> ORGANISM: Homo sapiens

<400> SEQUENCE: 2
caucuuuggu g                                                            11

<210> SEQ ID NO 3
<211> LENGTH: 19
<212> TYPE: DNA
<213> ORGANISM: Homo sapiens

<400> SEQUENCE: 3
gggagaactg gagccttca                                                    19

<210> SEQ ID NO 4
<211> LENGTH: 30
<212> TYPE: DNA
<213> ORGANISM: Homo sapiens

<400> SEQUENCE: 4
gtatctatat tcatcatagg aaacaccaca                                        30

<210> SEQ ID NO 5
<211> LENGTH: 30
<212> TYPE: DNA
<213> ORGANISM: Homo sapiens

<400> SEQUENCE: 5
gtatctatat tcatcatagg aaacaccatt                                        30

<210> SEQ ID NO 6
<211> LENGTH: 30
<212> TYPE: DNA
<213> ORGANISM: Homo sapiens

<400> SEQUENCE: 6
gcctggcacc attaaagaaa atatcatctt                                        30

<210> SEQ ID NO 7
<211> LENGTH: 30
<212> TYPE: DNA
```

```
<213> ORGANISM: Homo sapiens

<400> SEQUENCE: 7
gcctggcacc attaaagaaa atatcattgg                               30

<210> SEQ ID NO 8
<211> LENGTH: 24
<212> TYPE: DNA
<213> ORGANISM: Homo sapiens

<400> SEQUENCE: 8
gttggcatgc tttgatgacg cttc                                    24

<210> SEQ ID NO 9
<211> LENGTH: 26
<212> TYPE: DNA
<213> ORGANISM: Homo sapiens

<400> SEQUENCE: 9
ggcaccatta aagaaaatat catctt                                  26

<210> SEQ ID NO 10
<211> LENGTH: 26
<212> TYPE: DNA
<213> ORGANISM: Homo sapiens

<400> SEQUENCE: 10
ggcaccatta aagaaaatat cattgg                                  26

<210> SEQ ID NO 11
<211> LENGTH: 24
<212> TYPE: DNA
<213> ORGANISM: Homo sapiens

<400> SEQUENCE: 11
gttggcatgc tttgatgacg cttc                                    24

<210> SEQ ID NO 12
<211> LENGTH: 30
<212> TYPE: DNA
<213> ORGANISM: Homo sapiens

<400> SEQUENCE: 12
gcctggcacc attaaagaaa atatcatctt                              30

<210> SEQ ID NO 13
<211> LENGTH: 30
<212> TYPE: DNA
<213> ORGANISM: Homo sapiens

<400> SEQUENCE: 13
gcctggcacc attaaagaaa atatcattgg                              30

<210> SEQ ID NO 14
<211> LENGTH: 18
<212> TYPE: DNA
<213> ORGANISM: Homo sapiens

<400> SEQUENCE: 14
cagcttttcc tgggtcgc                                           18

<210> SEQ ID NO 15
<211> LENGTH: 33
```

```
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is a, c, g, or t

<400> SEQUENCE: 15
ggccttcatc agnttttagg tcgccatggc ggt                              33

<210> SEQ ID NO 16
<211> LENGTH: 8
<212> TYPE: RNA
<213> ORGANISM: Homo sapiens

<400> SEQUENCE: 16 accuaaaa                                                           8

<210> SEQ ID NO 17
<211> LENGTH: 12
<212> TYPE: RNA
<213> ORGANISM: Homo sapiens

<400> SEQUENCE: 17
gcugacagcc cu                                                     12

<210> SEQ ID NO 18
<211> LENGTH: 13
<212> TYPE: RNA
<213> ORGANISM: Homo sapiens

<400> SEQUENCE: 18
gcucgucgcu guc                                                    13

<210> SEQ ID NO 19
<211> LENGTH: 31
<212> TYPE: RNA
<213> ORGANISM: Homo sapiens

<400> SEQUENCE: 19
ccacuggcug acagcgacga gcccugaggg u                                31

<210> SEQ ID NO 20
<211> LENGTH: 19
<212> TYPE: DNA
<213> ORGANISM: Homo sapiens

<400> SEQUENCE: 20
atctgtggtg tttcctatg                                              19

<210> SEQ ID NO 21
<211> LENGTH: 33
<212> TYPE: RNA
<213> ORGANISM: Homo sapiens

<400> SEQUENCE: 21
aaagaaaaua ucaucuuugg uguuccuau gau                               33

<210> SEQ ID NO 22
<211> LENGTH: 30
<212> TYPE: RNA
<213> ORGANISM: Homo sapiens

<400> SEQUENCE: 22
```

```
aaagaaaaua ucauuggugu uuccuaugau                              30

<210> SEQ ID NO 23
<211> LENGTH: 39
<212> TYPE: RNA
<213> ORGANISM: Homo sapiens

<400> SEQUENCE: 23 gguucaacu gcggaaacuc uaaguuugga uuuggggc                      39

<210> SEQ ID NO 24
<211> LENGTH: 10
<212> TYPE: RNA
<213> ORGANISM: Homo sapiens

<400> SEQUENCE: 24
aaacagagcc                                                    10

<210> SEQ ID NO 25
<211> LENGTH: 14
<212> TYPE: RNA
<213> ORGANISM: Homo sapiens

<400> SEQUENCE: 25
gguuucaacu gcgg                                               14

<210> SEQ ID NO 26
<211> LENGTH: 14
<212> TYPE: RNA
<213> ORGANISM: Homo sapiens

<400> SEQUENCE: 26
uuggauuugg gggc                                               14

<210> SEQ ID NO 27
<211> LENGTH: 11
<212> TYPE: RNA
<213> ORGANISM: Homo sapiens
<220> FEATURE:
<221> NAME/KEY: misc_feature
<222> LOCATION: (1)..(1)
<223> OTHER INFORMATION: A is modified by a terminal phosphate group
<220> FEATURE:
<221> NAME/KEY: misc_feature
<222> LOCATION: (11)..(11)
<223> OTHER INFORMATION: U is modified by a terminal phosphate group

<400> SEQUENCE: 27
aaacuguaag u                                                  11

<210> SEQ ID NO 28
<211> LENGTH: 32
<212> TYPE: DNA
<213> ORGANISM: Homo sapiens

<400> SEQUENCE: 28
cccaaatcca aactacagtt tccgcagttg aa                           32

<210> SEQ ID NO 29
<211> LENGTH: 39
<212> TYPE: RNA
<213> ORGANISM: Homo sapiens
<220> FEATURE:
<221> NAME/KEY: misc_feature
<222> LOCATION: (15)..(15)
<223> OTHER INFORMATION: A is modified by a terminal phosphate group
```

```
<220> FEATURE:
<221> NAME/KEY: misc_feature
<222> LOCATION: (25)..(25)
<223> OTHER INFORMATION: U is modified by a terminal phosphate group

<400> SEQUENCE: 29 gguucaacu gcggaaacug uaaguuugga uuuggggc                               39

<210> SEQ ID NO 30
<211> LENGTH: 33
<212> TYPE: DNA
<213> ORGANISM: Homo sapiens

<400> SEQUENCE: 30
cccaaatcca aacttacagt ttccgcagtt gaa                                   33

<210> SEQ ID NO 31
<211> LENGTH: 39
<212> TYPE: RNA
<213> ORGANISM: Homo sapiens

<400> SEQUENCE: 31 gguucaacu gcggaaacug uaaguuugga uuuggggc                               39

<210> SEQ ID NO 32
<211> LENGTH: 39
<212> TYPE: RNA
<213> ORGANISM: Homo sapiens

<400> SEQUENCE: 32 gguucaacu gcggaaacuc uaaguuugga uuuggggc                               39

<210> SEQ ID NO 33
<211> LENGTH: 33
<212> TYPE: DNA
<213> ORGANISM: Homo sapiens

<400> SEQUENCE: 33
cccaaatcca aacttacagt ttccgcagtt gaa                                   33

<210> SEQ ID NO 34
<211> LENGTH: 11
<212> TYPE: RNA
<213> ORGANISM: Homo sapiens
<220> FEATURE:
<221> NAME/KEY: misc_feature
<222> LOCATION: (1)..(1)
<223> OTHER INFORMATION: A is modified by a terminal phosphate group
<220> FEATURE:
<221> NAME/KEY: misc_feature
<222> LOCATION: (11)..(11)
<223> OTHER INFORMATION: U is modified by a terminal phosphate group

<400> SEQUENCE: 34
aaacuguaag u                                                          11

<210> SEQ ID NO 35
<211> LENGTH: 39
<212> TYPE: RNA
<213> ORGANISM: Homo sapiens

<400> SEQUENCE: 35 gguucaacu gcggaaacug uaaguuugga uuuggggc                               39

<210> SEQ ID NO 36
```

```
<211> LENGTH: 14
<212> TYPE: DNA
<213> ORGANISM: Homo sapiens

<400> SEQUENCE: 36
aaacaccaat gata                                                        14

<210> SEQ ID NO 37
<211> LENGTH: 26
<212> TYPE: RNA
<213> ORGANISM: Homo sapiens

<400> SEQUENCE: 37
aaagaaaaua ucauguuucc uaugau                                           26

<210> SEQ ID NO 38
<211> LENGTH: 33
<212> TYPE: RNA
<213> ORGANISM: Homo sapiens

<400> SEQUENCE: 38
aucauaggaa acaccaaaga ugauauuuuc uuu                                   33

<210> SEQ ID NO 39
<211> LENGTH: 11
<212> TYPE: RNA
<213> ORGANISM: Homo sapiens
<220> FEATURE:
<221> NAME/KEY: misc_feature
<222> LOCATION: (1)..(1)
<223> OTHER INFORMATION: C is modified by a terminal phosphate group
<220> FEATURE:
<221> NAME/KEY: misc_feature
<222> LOCATION: (11)..(11)
<223> OTHER INFORMATION: G is modified by a terminal phosphate group

<400> SEQUENCE: 39
caucuuuggu g                                                           11

<210> SEQ ID NO 40
<211> LENGTH: 33
<212> TYPE: RNA
<213> ORGANISM: Homo sapiens

<400> SEQUENCE: 40
aaagaaaaua ucaucuuugg uguuuccuau gau                                   33

<210> SEQ ID NO 41
<211> LENGTH: 33
<212> TYPE: RNA
<213> ORGANISM: Homo sapiens

<400> SEQUENCE: 41
aucauaggaa acaccaaaga ugauauuuuc uuu                                   33

<210> SEQ ID NO 42
<211> LENGTH: 33
<212> TYPE: RNA
<213> ORGANISM: Homo sapiens

<400> SEQUENCE: 42
aaagaaaaua ucaucuuugg uguuuccuau gau                                   33

<210> SEQ ID NO 43
<211> LENGTH: 42
```

```
<212> TYPE: RNA
<213> ORGANISM: Homo sapiens

<400> SEQUENCE: 43
cgggagaccg ccauggcgac ccuggaaaag cugaugaagg cc                    42

<210> SEQ ID NO 44
<211> LENGTH: 42
<212> TYPE: DNA
<213> ORGANISM: Homo sapiens

<400> SEQUENCE: 44
ggccttcatc agcttttcca gggtcgccat ggcggtctcc cg                    42

<210> SEQ ID NO 45
<211> LENGTH: 18
<212> TYPE: RNA
<213> ORGANISM: Homo sapiens

<400> SEQUENCE: 45
cgggagaccg ccauggcg                                               18

<210> SEQ ID NO 46
<211> LENGTH: 12
<212> TYPE: RNA
<213> ORGANISM: Homo sapiens

<400> SEQUENCE: 46
cugaugaagg cc                                                     12

<210> SEQ ID NO 47
<211> LENGTH: 38
<212> TYPE: RNA
<213> ORGANISM: Homo sapiens

<400> SEQUENCE: 47
cgggagaccg ccauggcgac cuaaaacuga ugaaggcc                         38

<210> SEQ ID NO 48
<211> LENGTH: 42
<212> TYPE: RNA
<213> ORGANISM: Homo sapiens

<400> SEQUENCE: 48
cgggagaccg ccauggcgac ccuggaaaag cugaugaagg cc                    42

<210> SEQ ID NO 49
<211> LENGTH: 39
<212> TYPE: RNA
<213> ORGANISM: Homo sapiens
<220> FEATURE:
<221> NAME/KEY: misc_feature
<222> LOCATION: (27)..(27)
<223> OTHER INFORMATION: n is a, c, g, or u

<400> SEQUENCE: 49
cgggagaccg ccauggcgac cuaaaancug augaaggcc                        39

<210> SEQ ID NO 50
<211> LENGTH: 36
<212> TYPE: DNA
<213> ORGANISM: Homo sapiens

<400> SEQUENCE: 50
```

-continued agcaggaccc tcagggctgt cagccagtgg gatgca                36

<210> SEQ ID NO 51
<211> LENGTH: 36
<212> TYPE: DNA
<213> ORGANISM: Homo sapiens

<400> SEQUENCE: 51
tgcatcccac tggctgacag ccctgagggt cctgct                36

<210> SEQ ID NO 52
<211> LENGTH: 40
<212> TYPE: DNA
<213> ORGANISM: Homo sapiens

<400> SEQUENCE: 52
aggaccctca gggctcgtcg ctgtcagcca gtgcgatgca            40

<210> SEQ ID NO 53
<211> LENGTH: 40
<212> TYPE: DNA
<213> ORGANISM: Homo sapiens

<400> SEQUENCE: 53
tgcatcgcac tggctgacag cgacgagccc tgagggtcct            40

<210> SEQ ID NO 54
<211> LENGTH: 36
<212> TYPE: RNA
<213> ORGANISM: Homo sapiens

<400> SEQUENCE: 54
agcaggaccc ucagggcugu cagccagugg gaugca                36

<210> SEQ ID NO 55
<211> LENGTH: 15
<212> TYPE: DNA
<213> ORGANISM: Homo sapiens

<400> SEQUENCE: 55
agcaggaccc tcagg                                       15

<210> SEQ ID NO 56
<211> LENGTH: 15
<212> TYPE: DNA
<213> ORGANISM: Homo sapiens

<400> SEQUENCE: 56
agccagtggg atgca                                       15

<210> SEQ ID NO 57
<211> LENGTH: 43
<212> TYPE: RNA
<213> ORGANISM: Homo sapiens

<400> SEQUENCE: 57
agcaggaccc ucagggcucg ucgcugucag ccagugggau gca        43

<210> SEQ ID NO 58
<211> LENGTH: 31
<212> TYPE: RNA
<213> ORGANISM: Homo sapiens

<400> SEQUENCE: 58

```
aaagaaaaua caauguggug uuuccuauga u                                31
```

<210> SEQ ID NO 59
<211> LENGTH: 30
<212> TYPE: RNA
<213> ORGANISM: Homo sapiens

<400> SEQUENCE: 59

```
aaagaaaaua ucaucugugu uuccuaugau                                  30
```

<210> SEQ ID NO 60
<211> LENGTH: 33
<212> TYPE: RNA
<213> ORGANISM: Homo sapiens

<400> SEQUENCE: 60

```
aaagaaaaua ucaucugugg uguuuccuau gau                              33
```